(12) United States Patent
Floyd et al.

(10) Patent No.: US 9,797,021 B2
(45) Date of Patent: Oct. 24, 2017

(54) COMPOSITIONS COMPRISING C5 AND C6 OLIGOSACCHARIDES

(71) Applicant: Renmatix, Inc., King of Prussia, PA (US)

(72) Inventors: Daniel Clay Floyd, Richmond, VA (US); Kiran Kadam, Golden, CO (US); Srinivas Kilambi, Duluth, GA (US)

(73) Assignee: Renmatix, Inc., King of Prussia, PA (US)

(*) Notice: Subject to any disclaimer, the term of this patent is extended or adjusted under 35 U.S.C. 154(b) by 0 days.

(21) Appl. No.: 14/660,988

(22) Filed: Mar. 18, 2015

(65) Prior Publication Data

US 2015/0191499 A1 Jul. 9, 2015

Related U.S. Application Data

(63) Continuation of application No. 13/649,294, filed on Oct. 11, 2012, now abandoned.

(60) Provisional application No. 61/581,890, filed on Dec. 30, 2011, provisional application No. 61/581,907, filed on Dec. 30, 2011, provisional application No. 61/581,922, filed on Dec. 30, 2011, provisional application No. 61/581,878, filed on Dec. 30, 2011.

(51) Int. Cl.

| | |
|---|---|
| *C13K 1/02* | (2006.01) |
| *C13B 50/00* | (2011.01) |
| *C13K 13/00* | (2006.01) |
| *C13K 11/00* | (2006.01) |
| *C13K 1/04* | (2006.01) |
| *C07H 3/06* | (2006.01) |
| *C07H 3/02* | (2006.01) |

(52) U.S. Cl.
CPC ............... *C13K 1/02* (2013.01); *C07H 3/02* (2013.01); *C07H 3/06* (2013.01); *C13B 50/00* (2013.01); *C13K 1/04* (2013.01); *C13K 11/00* (2013.01); *C13K 13/00* (2013.01); *C13K 13/002* (2013.01); *C13K 13/007* (2013.01); *Y02E 50/16* (2013.01)

(58) Field of Classification Search
None
See application file for complete search history.

(56) References Cited

U.S. PATENT DOCUMENTS

| | | | |
|---|---|---|---|
| 3,990,904 A | 11/1976 | Friese et al. ............... 127/37 |
| 4,105,467 A | 8/1978 | Buckl et al. .............. 127/37 |
| 4,165,240 A | 8/1979 | Enokizono et al. ......... 127/29 |
| 4,445,938 A | 5/1984 | Verwaerde et al. | |
| 5,370,997 A | 12/1994 | Antranikian et al. | |
| 5,424,417 A * | 6/1995 | Torget ................... C08H 8/00 127/1 |
| 5,705,369 A | 1/1998 | Torget et al. ............. 435/105 |
| 5,980,640 A | 11/1999 | Nurmi et al. .............. 127/60 |
| 6,022,419 A | 2/2000 | Torget et al. .............. 127/37 |
| 6,086,681 A | 7/2000 | Lindroos et al. ........... 127/37 |
| 6,872,316 B2 | 3/2005 | Heikkila et al. | |
| 7,026,152 B2 | 4/2006 | Ingram et al. ............. 435/210 |
| 8,030,039 B1 | 10/2011 | Retsina et al. | |
| 8,894,771 B2 | 11/2014 | Floyd et al. | |
| 9,243,303 B2 * | 1/2016 | Fang ..................... C13K 1/02 |
| 9,617,608 B2 | 4/2017 | Eyal et al. | |
| 2002/0153317 A1 | 10/2002 | Heikkila et al. | |
| 2002/0159990 A1 | 10/2002 | Ingram et al. | |
| 2005/0069998 A1 | 3/2005 | Ballesteros Perdices et al. | |
| 2005/0244934 A1 | 11/2005 | Foody et al. | |
| 2006/0281913 A1 | 12/2006 | Ferreira et al. | |
| 2007/0254348 A1 | 11/2007 | Retsina et al. | |
| 2007/0274955 A1 | 11/2007 | Glenn et al. | |
| 2008/0102502 A1 | 5/2008 | Foody et al. | |
| 2008/0292766 A1 | 11/2008 | Hoffman et al. | |
| 2009/0176979 A1 | 7/2009 | Hara et al. | |
| 2009/0215718 A1 | 8/2009 | van Laere et al. | |
| 2009/0232892 A1 | 9/2009 | Yamasaki et al. | |
| 2010/0043782 A1 | 2/2010 | Kilambi et al. | |
| 2010/0069626 A1 | 3/2010 | Kilambi et al. | |
| 2010/0136634 A1 | 6/2010 | Kratochvil et al. | |
| 2010/0170504 A1 | 7/2010 | Zhang | |
| 2010/0184151 A1 | 7/2010 | Tolan et al. | |
| 2010/0203605 A1 | 8/2010 | Kim et al. | |
| 2010/0297704 A1 | 11/2010 | Li | |
| 2011/0061645 A1 | 3/2011 | Fosdick et al. | |
| 2011/0183394 A1 | 7/2011 | Bell et al. | |
| 2012/0116063 A1 | 5/2012 | Jansen et al. | |
| 2012/0282655 A1 | 11/2012 | Gibbs | |
| 2012/0289692 A1 | 11/2012 | Gray et al. | |

(Continued)

FOREIGN PATENT DOCUMENTS

| | | |
|---|---|---|
| CA | 1060824 A | 8/1979 |
| CN | 1353310 A | 6/2002 |

(Continued)

OTHER PUBLICATIONS

Gullón, B., Yáñez, R., Alonso, J. L., & Parajó, J. C. (2010). Production of oligosaccharides and sugars from rye straw: a kinetic approach. Bioresource technology, 101(17), 6676-6684.*

Sun, R., Fang, J. M., & Tomkinson, J. (2000). Characterization and esterification of hemicelluloses from rye straw. Journal of agricultural and food chemistry, 48(4), 1247-1252.*

Chandel, et al., "Detoxification of Lignocellulosic Hydrolysates for Improved Bioethanol Production," Biofuel Production—Recent Developments and Prospects, Sep. 1, 2011, pp. 225-246.

Martinez, et al., "Detoxification of dilute acid hydrolysates of lignocellulose with lime," Biotechnology Progress, American Institute of Chemical Engineers, vol. 17, Jan. 1, 2001, pp. 287-293.

Zhao et al., "Fermentable hexose production from corn stalks and wheat straw with combined supercritical and subcritical hydrothermal technology", Bioscience Technology, vol. 100, Jul. 18, 2009, pp. 5884-5889.

(Continued)

*Primary Examiner* — Shaojia Anna Jiang
*Assistant Examiner* — Dale R Miller
(74) *Attorney, Agent, or Firm* — Travis B. Gasa; Andrew G. Bunn; Ballard Spahr LLP

(57) ABSTRACT

Compositions comprising C5 and C6 saccharides of varying degrees of polymerization and low levels of undesirable impurities, such as compounds containing sulfur, nitrogen, or metals, are disclosed.

38 Claims, 4 Drawing Sheets

(56) References Cited

U.S. PATENT DOCUMENTS

| | | |
|---|---|---|
| 2016/0108481 A1 | 4/2016 | Eyal et al. |
| 2016/0108482 A1 | 4/2016 | Eyal et al. |

FOREIGN PATENT DOCUMENTS

| | | |
|---|---|---|
| CN | 1505682 A | 6/2004 |
| CN | 101613970 | 12/2009 |
| DE | 1955392 A1 | 6/1971 |
| EP | 814676 | 1/1998 |
| EP | 1304412 | 4/2003 |
| JP | S5141451 A | 4/1976 |
| JP | 62-283988 | 12/1987 |
| JP | 2835894 B2 | 12/1998 |
| JP | 2002-177000 A | 6/2002 |
| JP | 2005-023041 A | 1/2005 |
| JP | 2006-101829 A | 4/2006 |
| JP | 2006-223152 A | 8/2006 |
| JP | 2008-035853 | 2/2008 |
| JP | 2011-103874 A | 6/2011 |
| RU | 2313572 C2 | 12/2007 |
| WO | WO 00/61276 | 10/2000 |
| WO | WO 01/32715 | 5/2001 |
| WO | WO 2004/013409 | 2/2004 |
| WO | WO 2009/060126 | 5/2009 |
| WO | WO-2009/137839 A1 | 11/2009 |
| WO | WO-2009/0154447 A1 | 12/2009 |
| WO | WO-2010009343 A2 | 1/2010 |
| WO | WO 2010/045576 | 4/2010 |
| WO | WO 2010/046532 | 4/2010 |
| WO | WO 2011/091044 | 7/2011 |
| WO | WO-2011091044 A1 | 7/2011 |
| WO | WO 2013/055785 | 10/2012 |
| WO | WO-2013/055785 A1 | 4/2013 |
| WO | WO 2013/070969 | 5/2013 |

OTHER PUBLICATIONS

Zhao et al., "Supercritical hydrolysis of cellulose for oligosaccharide production in combined technology", Chemical Engineering Journal, vol. 150, Aug. 31, 2009, pp. 411-417.
Extended European Search Report issued on Aug. 31, 2015 for application 12863319.5, filed on Dec. 3, 2012, and published as EP 2797944 on Nov. 5, 2014 (Applicant—Renmatix, Inc. // Inventor—Floyd, et al.,) (8 pages).
Extended European Search Report issued on Sep. 8, 2015 for application 12861480.7, filed on Dec. 3, 2012, and published as EP 2797943 on Nov. 5, 2014 (Applicant—Renmatix, Inc. // Inventor—Floyd, et al.,) (7 pages).
"SCHARLAU Technical Data Sheet Product Code GL0125 D(+)—Giucose anhydrous, extra pure, Ph Eur, USP, BP", 2006, 1 page.
"SCHARLAU Technical Data Sheet Product Code LE0070 D(-31 )—Fructose, extra pure, Ph Eur, USP, BP, FCC", Jun. 2006, 1 page.
"Standard Test Method for Sulfated Ash from Lubricating Oils and Additives", ASTM D874-13a, retrieved from the internet at least as early as Oct. 11, 2013, http://www.astm.org/Standards/D874.htm, 2 pages.
Buranov, A. et al. (201 0). Extraction and characterization of hemicelluloses from flax shives by different methods. Carbohydrate polymers, 79(1 ), 17-25.
Cacace, J. et al. (2006). Pressurized low polarity water extraction of lignans from whole flaxseed. Journal of Food Engineering, 77(4), 1087-1095.
Cox, M. et al. (1999). Preparation and characterisation of a carbon adsorbent from flax shive by dehydration with sulfuric acid. Journal of Chemical Technology and Biotechnology, 74(11 ), 1019-1029.
Enzyme Technology, "Glucose from Cellulose", retrieved from the internet at least as early as Oct. 7, 2013, http://www.lsbu.ac.uk/water/enztech/cellulose.html, 2 pages.
Finney N. "Essentials of Glycobiology", pp. 1-26; Apr. 2004 http://grtc.ucsd.edu/oldessentials/2004/lecture.pdf.
Hu, et al. The direct conversion of xylan to lactic acid by lactobacillus brevis transformed with a xylanase gene. Green Chem., vol. 13(7), pp. 1729-1734 (2011).
Ioannidou et al., "Direct determination of toxic trace metals in honey and sugars using inductively coupled plasma atomic emission spectrometry," Talanta, 65(1): 92-97 (2005).
Kelkone Lev Ai, "Atom spectrometric methods for determination of trace metal impurities in pharmaceutical substances," Acta Pharmaceutica Hungarica, 71 (3): 350-356 (2001 ).
Korean Intellectual Property Office, "International Search Report and Written Opinion" in International Application No. PCT/US2012/067641 (Mar. 13, 2013).
Lu, X. et al. (2010). Hydrolysis of Japanese beech by batch and semi-flow water under subcritical temperatures and pressures. Biomass and bioenergy, 34(8), 1 089-1 097.
Miller-Ihli et al., "Direct determination of lead in sugars using graphite furnace atomic absorption spectrometry," Atomic Spectroscopy, 14(4): 85-89 (1993).
Napradean et al., "Studies regarding cadmium determination by atomic absorption spectrometry. Note II. Pharmaceutical finished products," Farmacia, 53(2): 86-90 (Bucharest, Romania, 2005).
Pohl et al., "Direct Determination of the Total Concentrations of Magnesium, Calcium, Manganese, and Iron in Addition to their Chemical and Physical Fractions in Dark Honeys," Anal. Lett., 44(13): 2265-2279 (2011 ).
Ranatunga, T. et al. (2000). The effect of overliming on the toxicity of dilute acid pretreated lignocellulosics: the role of inorganics, uronic acids and ether-soluble organics. Enzyme and microbial technology, 27(3), 240-247.
Sasaki et al., "Dissolution and Hydrolysis of Cellulose in Subcritical and Supercritical Water", Industrial & Engineering Chemistry Research, 39(8), 2000, pp. 2883-2890.
Scharlab, "Scharlau Certificate of Analysis for Product MA0100," Scharlab, S.L., Batch 14702001, Sep. 10, 2013.
Scharlab, "Scharlau Certificate of Analysis for Product X10080," Scharlab, S.L., Batch 15335702, May 7, 2014.
Scharlau®, "Technical Data Sheet—Product code: XI0080, D(+)—Xylose, extra pure, Ph, Eur, BP," (Jun. 2006).
Schenk, "Glucose and Glucose-Containing Syrups", Ullmann's Encyclopedia of Industrial Chemistry, vol. 17, http://www.dx.doi.org/1 0.1002%2F14356007.a12_457.pub2, 2006, pp. 45-66.
Terol et al., "High-Temperature Liquid Chromatography Inductively Coupled Plasma Atomic Emission Spectrometry hyphenation for the combined organic and inorganic analysis of foodstuffs," J. Chromatography, 1217(40): 6195-6202 (2010).
Thomas, R., Practical Guide to ICP-MS: A Tutorial for Beginners, Second Edition, CRC Press 2008, Print ISBN: 978-1-4200-6786-6.
Vassilev et al., "An Overview of the Chemical Composition of Biomass", Fuel 89, 2010, pp. 913-933.
Veres et al., "Studies on matrix effects in the determination of the metal content of sugar complexes by atomic absorption spectrometry," Magyar Kemiai Folyoirat, 93(5): 199-204 (1987).
Winter, F. et al. (1999). NO and N< sub> 2</sub> 0 formation during the combustion of wood, straw, malt waste and peat. Bioresource Technology, 70(1 ), 39-49.
Wu et al., "Determination of trace calcium in glucose by Zeeman flame atomic absorption spectrometry," Guangdong Weiliang Yuansu Kexue, 14(3): 58-60 (2007).
Zhang et al., "Cellodextrin preparation by mixed-acid hydrolysis and chromatographic separation", Analytical Biochemistry, 322(2), 2003, pp. 225-232.
Applicant-Initiated Interview Summary issued on Oct. 17, 2013 for U.S. Appl. No. 13/649,395, filed Oct. 11, 2012 (Applicant—Renmatix, Inc.; Inventors—Floyd, et al.; (3 pages).
Applicant-Initiated Interview Summary issued on Oct. 21, 2013 for U.S. Appl. No. 13/349,437, filed Oct. 11, 2012 (Applicant—Renmatix, Inc.; Inventors—Floyd, et al.; (3 pages).
International Preliminary Report on Patentability issued Jul. 1, 2014 for International Patent Application No. PCT/US2012/067537, which was filed on Dec. 3, 2012 and published as WO 2013/101398 on Jul. 4, 2013 (Inventor—Floyd; Applicant—Renmatix, Inc.; (pp. 1-7).
International Preliminary Report on Patentability issued Jul. 1, 2014 for International Patent Application No. PCT/US2012/067538,

(56) References Cited

OTHER PUBLICATIONS which was filed on Dec. 3, 2012 and published as WO 2013/101399 on Jul. 4, 2013 (Inventor—Floyd; Applicant—Renmatix, Inc.; (pp. 1-7).
International Preliminary Report on Patentability issued Jul. 1, 2014 for International Patent Application No. PCT/US2012/067641, which was filed on Dec. 3, 2012 and published as WO 2013/101402 on Jul. 4, 2013 (Inventor—Floyd; Applicant—Renmatix, Inc.; (pp. 1-9).
International Preliminary Report on Patentability issued Jul. 1, 2014 for International Patent Application No. PCT/US2012/067644, which was filed on Jul. 4, 2013 and published as WO 2013/101403 on Jul. 4, 2013 (Inventor—Floyd; Applicant—Renmatix, Inc.; (pp. 1-9).
International Preliminary Report on Patentability issued Jul. 1, 2014 for International Patent Application No. PCTIUS2012/067538, which was filed on Dec. 3, 2012 and published as WO 2013/101399 on Jul. 4, 2013 (Inventor—Floyd; Applicant—Renmatix, Inc.; (pp. 1-7).
International Preliminary Report on Patentability issued Jul. 1, 2014 for International Patent Application No. PCTIUS2012/067641, which was filed on Dec. 3, 2012 and published as WO 2013/101402 on Jul. 4, 2013 (Inventor—Floyd; Applicant—Renmatix, Inc.; (pp. 1-9).
International Preliminary Report on Patentability issued Jul. 1, 2014 for International Patent Application No. PCTIUS2012/067644, which was filed on Jul. 4, 2013 and published as WO 2013/101403 on Jul. 4, 2013 (Inventor—Floyd; Applicant—Renmatix, Inc.; (pp. 1-9).
Korean Intellectual Property Office, "International Search Report and Written Opinion" in International Patent Application No. PCT/US2012/067538 (Mar. 18, 2013).
Korean Intellectual Property Office, "International Search Report and Written Opinion" in International Patent Application No. PCT/US2012/067644 (Mar. 13, 2013).
Non-Final Rejection issued Nov. 17, 2014 for U.S. Appl. No. 13/649,437, filed on Oct. 11, 2012 and published as US 2013-0167837 on Jul. 4, 2013 (Inventor—Floyd; Applicant—Renmatix, Inc.; (pp. 1-6).
Notice of Allowance issued Jul. 24, 2014 for U.S. Appl. No. 13/649,437, filed Oct. 11, 2012 and published as US 2013/0167837 on Jul. 4, 2013 (Inventor—Floyd; Applicant—Renmatix, Inc.; (pp. 1-5).
Notice of Allowance issued Sep. 5, 2014 for U.S. Appl. No. 13/649,395, filed Oct. 11, 2012 and published as US 2013/0167836 on Jul. 4, 2013 (Inventor—Floyd; Applicant—Renmatix, Inc.; (pp. 1-7).
Office Action issued Jul. 30, 2014 for Canadian Patent Application No. 2,804,993, which was filed on Dec. 3, 2012 (Inventor—Floyd; Applicant—Renmatix, Inc.; (pp. 1-3).
Office Action issued Jul. 30, 2014 for Canadian Patent Application No. 2,817,235, which was filed on Dec. 3, 2012 (Inventor—Floyd; Applicant—Renmatix, Inc.; (pp. 1-2).
Official Action issued on Oct. 1, 2013 for Canadian Patent Application No. 2,817,235 filed Dec. 3, 2012 (Applicant—Renmatix, Inc.; Inventors—Floyd, et al.; (3 pages).
Official Action issued on Oct. 4, 2013 for Canadian Patent Application No. 2,804,993 filed Dec. 3, 2012 (Applicant—Renmatix, Inc.; Inventors—Floyd, et al.; (3 pages).
Non Final Office Action mailed Jul. 16, 2013 for U.S. Appl. No. 13/649,437, filed Oct. 11, 2012 and published as US 2013-0167837 on Jul. 4, 2013 (Inventor—Floyd; Applicant—Renmatix, Inc.; (pp. 1-7).
Notice of Allowance issued Jan. 9, 2015 for U.S. Appl. No. 13/649,343, filed Oct. 11, 2012 and published as US 2013/0172547 on Jul. 4, 2013 (Inventor—Floyd; Applicant—Renmatix, Inc.; (17 pages).
Final Office Action issued Jul. 7, 2014 for U.S. Appl. No. 13/649,343, filed Oct. 11, 2012 and published as US 2013/0172547 on Jul. 4, 2013 (Inventor—Floyd; Applicant—Renmatix, Inc.; (23 pages).
Non Final Office Action issued Mar. 7, 2014 for U.S. Appl. No. 13/649,343, filed Oct. 11, 2012 and published as US 2013/0172547 on Jul. 4, 2013 (Inventor—Floyd; Applicant—Renmatix, Inc.; (23 pages).
Non Final Office Action issued Oct. 8, 2013 for U.S. Appl. No. 13/649,343, filed Oct. 11, 2012 and published as US 2013/0172547 on Jul. 4, 2013 (Inventor—Floyd; Applicant—Renmatix, Inc.; (18 pages).
Final Rejection issued Jul. 18, 2014 for U.S. Appl. No. 13/694,294, filed Oct. 11, 2012 and published as US 2013/0172546 on Jul. 4, 2013 (Inventor—Floyd; Applicant—Renmatix, Inc.; (20 pages).
Non-Final Rejection issued Mar. 3, 2014 for U.S. Appl. No. 13/694,294, filed Oct. 11, 2012 and published as US 2013/0172546 on Jul. 4, 2013 (Inventor—Floyd; Applicant—Renmatix, Inc.; (11 pages).
Non-Final Rejection issued Sep. 18, 2013 for U.S. Appl. No. 13/694,294, filed Oct. 11, 2012 and published as US 2013/0172546 on Jul. 4, 2013 (Inventor—Floyd; Applicant—Renmatix, Inc.; (17 pages).
Non-Final Office Action issued on Dec. 17, 2015 for U.S. Appl. No. 14/661,000, filed Mar. 18, 2015 and published as US-2015-0191500-A1 on Jul. 9, 2015 (Applicant—Renmatix, Inc. // Inventor—Floyd, et al.) (16 pages).
Miller-lhli, Trace Element Determination in Foods and Biological Samples Using Inductively Coupled lasma Atomic Emission Spectrometry and Flame Atomic Absorption Spectrometry. J Agric Food Chem. 1996; 44:2675-9.
Mupondwa, E. et al., Status of Canada's Lignocellulosic Ethanol: Part I: Pretreatment Technologies. Renew Sustainable Energy Rev. 2017; 72:178-90.

\* cited by examiner

COMPOSITIONS COMPRISING C5 AND C6 OLIGOSACCHARIDES

CROSS REFERENCE TO RELATED APPLICATIONS

This application is a continuation of application Ser. No. 13/649,294 filed Oct. 11, 2012, currently pending, which claims the benefit of:
U.S. Application No. 61/581,907 filed Dec. 30, 2011;
U.S. Application No. 61/581,922 filed Dec. 30, 2011;
U.S. Application No. 61/581,878 filed Dec. 30, 2011; and
U.S. Application No. 61/581,890 filed Dec. 30, 2011;
the entire disclosures of which are incorporated herein by reference.

FIELD OF THE INVENTION

The present invention generally relates to compositions comprising C5 and C6 saccharides of varying degrees of polymerization and/or containing maximum levels of undesirable impurities, such as compounds containing sulfur, nitrogen, or metals, especially those processed from lignocellulosic biomass using supercritical, subcritical, and/or near critical fluid extraction.

BACKGROUND OF THE INVENTION

There are a number of processes for converting lignocellulosic biomass into liquid streams of various fermentable sugars. Certain preferred processes are based on supercritical water (SCW) or hot compressed water (HCW) technology, which offer several advantages including high throughputs, use of mixed feedstocks, separation of sugars, and avoidance of concentrated acids, microbial cultures, and enzymes. Processes using hot compressed water may have two distinct operations: pre-treatment and cellulose hydrolysis. The pre-treatment process hydrolyzes the hemicellulose component of the lignocellulosic biomass and cellulose hydrolysis (CH) process, as its name infers, hydrolyzes the cellulose fibers. The resultant five carbon (C5) and six carbon (C6) sugar streams are recovered separately. The remaining solids, which consist mostly of lignin, are preferably recovered, such as through filtration, and may be used as a fuel to provide thermal energy to the process itself or for other processes.

Among their many uses, the sugar streams may be converted to ethanol through fermentation using yeast or bacteria that feed on the sugars. As the sugars are consumed, ethanol and carbon dioxide are produced.

The invention is directed to these compositions, as well as and other important ends.

SUMMARY OF THE INVENTION

In one embodiment, the invention is directed to compositions, comprising:
at least one water-soluble C6 oligosaccharide hydrolysate, especially those hydrolysates processed from lignocellulosic biomass using supercritical or near critical fluid extraction;
optionally, at least one water-soluble C6 monosaccharide hydrolysate; and
less than about 5250 ppm in total by weight, based on total weight of said water-soluble C6 oligosaccharide hydrolysate and said water-soluble C6 monosaccharide hydrolysate in said composition, of elements;
wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In another embodiment, the invention is directed to compositions, comprising:
at least one water-soluble C6 oligosaccharide hydrolysate, especially those hydrolysates processed from lignocellulosic biomass using supercritical or near critical fluid extraction;
optionally, at least one water-soluble C6 monosaccharide hydrolysate; and
less than about 10 ppm by weight, based on total weight of said water-soluble C6 oligosaccharide hydrolysate and said water-soluble C6 monosaccharide hydrolysate in said composition, of aluminum;
less than about 3000 ppm by weight, based on total weight of said water-soluble C6 oligosaccharide hydrolysate and said water-soluble C6 monosaccharide hydrolysate in said composition, of calcium;
less than about 350 ppm by weight, based on total weight of said water-soluble C6 oligosaccharide hydrolysate and said water-soluble C6 monosaccharide hydrolysate in said composition, of iron; and
less than about 1000 ppm by weight, based on total weight of said water-soluble C6 oligosaccharide hydrolysate and said water-soluble C6 monosaccharide hydrolysate in said composition, of sulfur.

In other embodiments, the invention is directed to compositions, comprising:
at least one water-soluble C6 oligosaccharide hydrolysate, especially those hydrolysates processed from lignocellulosic biomass using supercritical or near critical fluid extraction;
optionally, at least one water-soluble C6 monosaccharide hydrolysate; and
less than about 10 ppm by weight, based on total weight of said water-soluble C6 oligosaccharide hydrolysate and said water-soluble C6 monosaccharide hydrolysate in said composition, of aluminum.

In a further embodiment, the invention is directed to compositions, comprising:
at least one water-soluble C6 oligosaccharide hydrolysate, especially those hydrolysates processed from lignocellulosic biomass using supercritical or near critical fluid extraction;
optionally, at least one water-soluble C6 monosaccharide hydrolysate; and
less than about 3000 ppm by weight, based on total weight of said water-soluble C6 oligosaccharide hydrolysate and said water-soluble C6 monosaccharide hydrolysate in said composition, of calcium.

In yet other embodiments, the invention is directed to compositions, comprising:
at least one water-soluble C6 oligosaccharide hydrolysate, especially those hydrolysates processed from lignocellulosic biomass using supercritical or near critical fluid extraction;
optionally, at least one water-soluble C6 monosaccharide hydrolysate; and
less than about 350 ppm by weight, based on total weight of said water-soluble C6 oligosaccharide hydrolysate and said water-soluble C6 monosaccharide hydrolysate in said composition, of iron.

In another embodiment, the invention is directed to compositions, comprising:
at least one water-soluble C6 oligosaccharide hydrolysate, especially those hydrolysates processed from lignocellulosic biomass using supercritical or near critical fluid extraction;
optionally, at least one water-soluble C6 monosaccharide hydrolysate; and less than about 1000 ppm by weight, based on total weight of said water-soluble C6 oligosaccharide hydrolysate and said water-soluble C6 monosaccharide hydrolysate in said composition, of sulfur.

In yet another embodiment, the invention is directed to compositions, comprising:
about 10% by weight to about 25% by weight, based on total weight of C6 saccharides present in said composition, of C6 disaccharides;
about 10% by weight to about 25% by weight, based on total weight of C6 saccharides present in said composition, of C6 trisaccharides;
about 10% by weight to about 25% by weight, based on total weight of C6 saccharides present in said composition, of C6 tetrasaccharides;
about 10% by weight to about 25% by weight, based on total weight of C6 saccharides present in said composition, of C6 pentasaccharides; and
about 10% by weight to about 50% by weight, based on total weight of C6 saccharides present in said composition, of C6 saccharides having at a degree of polymerization of at least about 6.

In further embodiments, the invention is directed to compositions, comprising:
about 80% by weight to about 95% by weight, based on total weight of C6 saccharides present in said composition, of water-soluble C6 oligosaccharides;
wherein said water-soluble C6 oligosaccharides have a degree of polymerization of about 2 to about 15.

In other embodiments, the invention is directed to compositions, comprising:
at least one water-soluble C5 oligosaccharide hydrolysate, especially those hydrolysates processed from lignocellulosic biomass using supercritical or near critical fluid extraction;
optionally, at least one water-soluble C5 monosaccharide hydrolysate; and
less than about 3700 ppm in total by weight, based on total weight of said water-soluble C5 oligosaccharide hydrolysate and said water-soluble C5 monosaccharide hydrolysate in said composition, of elements;
wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In one embodiment, the invention is directed to compositions, comprising:
at least one water-soluble C5 oligosaccharide hydrolysate, especially those hydrolysates processed from lignocellulosic biomass using supercritical or near critical fluid extraction;
optionally, at least one water-soluble C5 monosaccharide hydrolysate; and
less than about 10 ppm by weight, based on the total weight of C5 saccharide hydrolysate in said composition, of aluminum;
less than about 2300 ppm by weight, based on the total weight of C5 saccharide hydrolysate in said composition, of calcium;
less than about 50 ppm by weight, based on the total weight of C5 saccharide hydrolysate in said composition, of iron; and
less than about 150 ppm by weight, based on the total weight of C5 saccharide hydrolysate in said composition, of sulfur.

In further embodiments, the invention is directed to compositions, comprising:
at least one water-soluble C5 oligosaccharide hydrolysate, especially those hydrolysates processed from lignocellulosic biomass using supercritical or near critical fluid extraction;
optionally, at least one water-soluble C5 monosaccharide hydrolysate; and
less than about 10 ppm, based on total weight of said water-soluble C5 oligosaccharide hydrolysate and said water-soluble C5 monosaccharide hydrolysate in said composition, of aluminum.

In yet further embodiments, the invention is directed to compositions, comprising:
at least one water-soluble C5 oligosaccharide hydrolysate, especially those hydrolysates processed from lignocellulosic biomass using supercritical or near critical fluid extraction;
optionally, at least one water-soluble C5 monosaccharide hydrolysate; and
less than about 2300 ppm by weight, based on total weight of said water-soluble C5 oligosaccharide hydrolysate and said water-soluble C5 monosaccharide hydrolysate in said composition, of calcium.

In another embodiment, the invention is directed to compositions, comprising:
at least one water-soluble C5 oligosaccharide hydrolysate, especially those hydrolysates processed from lignocellulosic biomass using supercritical or near critical fluid extraction;
optionally, at least one water-soluble C5 monosaccharide hydrolysate; and
less than about 50 ppm by weight, based on total weight of said water-soluble C5 oligosaccharide hydrolysate and said water-soluble C5 monosaccharide hydrolysate in said composition, of iron.

In yet another embodiment, the invention is directed to compositions, comprising:
at least one water-soluble C5 oligosaccharide hydrolysate, especially those hydrolysates processed from lignocellulosic biomass using supercritical or near critical fluid extraction;
optionally, at least one water-soluble C5 monosaccharide hydrolysate; and
less than about 150 ppm by weight, based on total weight of said water-soluble C5 oligosaccharide hydrolysate and said water-soluble C5 monosaccharide hydrolysate in said composition, of sulfur.

In certain embodiments, the invention is directed to methods of reducing the level of enzyme required for enzymatically hydrolyzing first water-soluble C6 saccharides having an average degree of polymerization to about 2 to about 15, preferably about 2 to about 10, and more preferably about 2 to about 6, to second water-soluble C6 saccharides having a lower average degree of polymerization than said average degree of polymerization of said first water-soluble C6 saccharides, comprising:
providing a hydrolysate comprising said first water-soluble C6 saccharides and less than about 5250 ppm in total, based on total weight of water-soluble C6 saccharide hydrolysate in said composition, of elements;
wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In certain embodiments, the invention is directed to methods of reducing the level of enzyme required for enzymatically hydrolyzing first water-soluble C5 saccharides having an average degree of polymerization to about 2 to about 28, preferably about 2 to about 15, more preferably about 2 to about 13, even more preferably about 2 to about 6, to second water-soluble C5 saccharides having a lower average degree of polymerization than said average degree of polymerization of said first water-soluble C5 saccharides, comprising:
providing a hydrolysate comprising said first water-soluble C5 saccharides and less than about 3700 ppm in total, based on total weight of water-soluble C5 saccharide hydrolysate in said composition, of elements;

wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE INVENTION

Figure 1A:
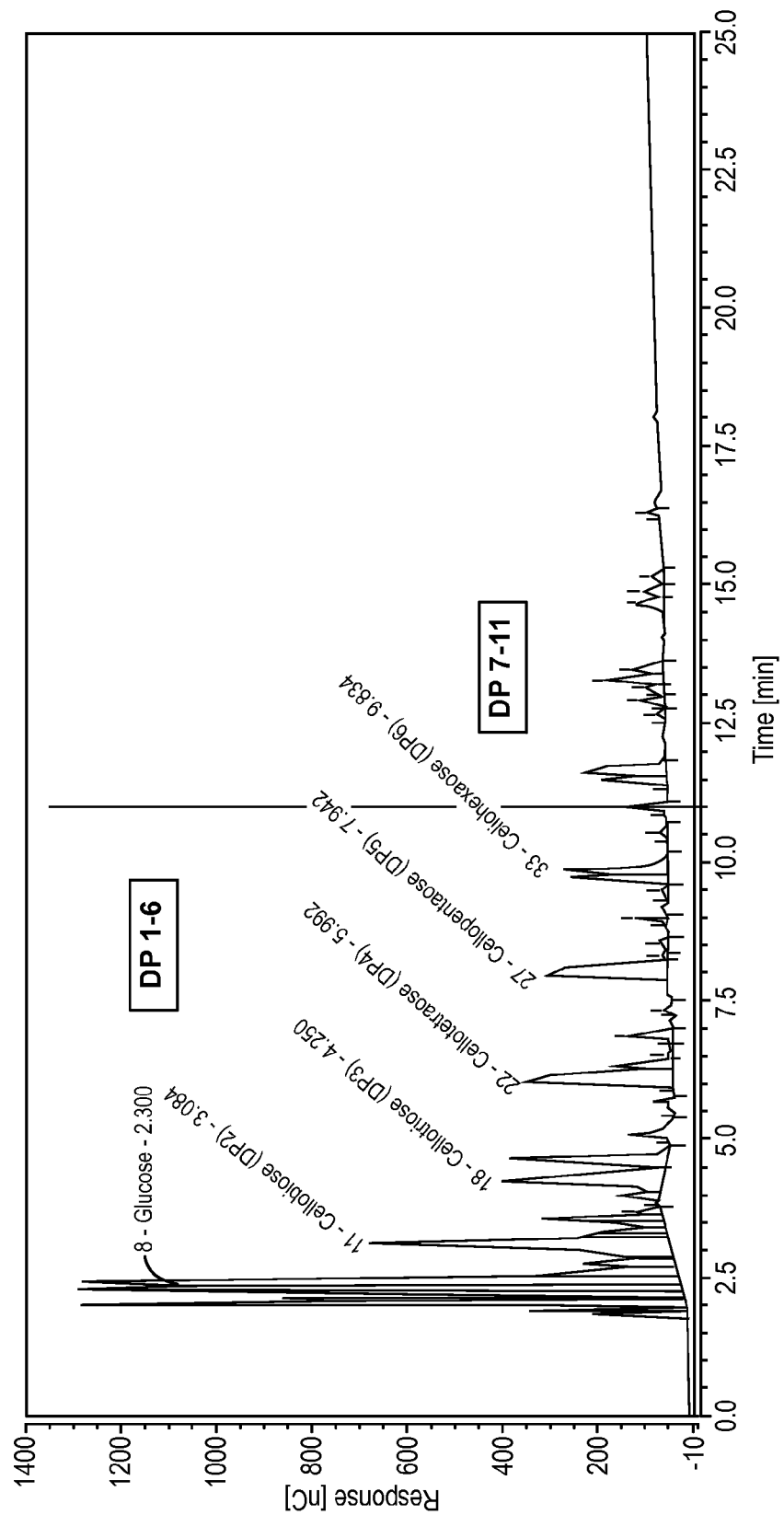
FIG. 1A is a scan from a DIONEX high pressure liquid chromatography device with an electrochemical detector of a C6 oligosaccharide composition of one embodiment of the invention.

As employed above and throughout the disclosure, the following terms, unless otherwise indicated, shall be understood to have the following meanings.

As used herein, the singular forms "a," "an," and "the" include the plural reference unless the context clearly indicates otherwise.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

As used herein, the phrase "substantially free" means have no more than about 1%, preferably less than about 0.5%, more preferably, less than about 0.1%, by weight of a component, based on the total weight of any composition containing the component.

A supercritical fluid is a fluid at a temperature above its critical temperature and at a pressure above its critical pressure. A supercritical fluid exists at or above its "critical point," the point of highest temperature and pressure at which the liquid and vapor (gas) phases can exist in equilibrium with one another. Above critical pressure and critical temperature, the distinction between liquid and gas phases disappears. A supercritical fluid possesses approximately the penetration properties of a gas simultaneously with the solvent properties of a liquid. Accordingly, supercritical fluid extraction has the benefit of high penetrability and good solvation.

Reported critical temperatures and pressures include: for pure water, a critical temperature of about 374.2° C., and a critical pressure of about 221 bar; for carbon dioxide, a critical temperature of about 31° C. and a critical pressure of about 72.9 atmospheres (about 1072 psig). Near critical water has a temperature at or above about 300° C. and below the critical temperature of water (374.2° C.), and a pressure high enough to ensure that all fluid is in the liquid phase. Sub-critical water has a temperature of less than about 300° C. and a pressure high enough to ensure that all fluid is in the liquid phase. Sub-critical water temperature may be greater than about 250° C. and less than about 300° C., and in many instances sub-critical water has a temperature between about 250° C. and about 280° C. The term "hot compressed water" is used interchangeably herein for water that is at or above its critical state, or defined herein as near-critical or sub-critical, or any other temperature above about 50° C. (preferably, at least about 100° C.) but less than subcritical and at pressures such that water is in a liquid state.

As used herein, a fluid which is "supercritical" (e.g. supercritical water, supercritical $CO_2$, etc.) indicates a fluid which would be supercritical if present in pure form under a given set of temperature and pressure conditions. For example, "supercritical water" indicates water present at a temperature of at least about 374.2° C. and a pressure of at least about 221 bar, whether the water is pure water, or present as a mixture (e.g. water and ethanol, water and $CO_2$, etc). Thus, for example, "a mixture of sub-critical water and supercritical carbon dioxide" indicates a mixture of water and carbon dioxide at a temperature and pressure above that of the critical point for carbon dioxide but below the critical point for water, regardless of whether the supercritical phase contains water and regardless of whether the water phase contains any carbon dioxide. For example, a mixture of sub-critical water and supercritical $CO_2$ may have a temperature of about 250° C. to about 280° C. and a pressure of at least about 225 bar.

As used herein, "lignocellulosic biomass or a component part thereof" refers to plant biomass containing cellulose, hemicellulose, and lignin from a variety of sources, including, without limitation (1) agricultural residues (including corn stover and sugarcane bagasse), (2) dedicated energy crops, (3) wood residues (including hardwoods, softwoods, sawmill and paper mill discards), and (4) municipal waste, and their constituent parts including without limitation, lignocellulose biomass itself, lignin, saccharides (including cellulose, cellobiose, $C_6$ oligosaccharides, $C_6$ monosaccharides, $C_5$ saccharides (including hemicellulose, $C_5$ oligosaccharides, and $C_5$ monosaccharides), and mixtures thereof.

As used herein, "ash" refers to the non-aqueous residue that remains after a sample is burned, and consists mostly of metal oxides. Ash content may be measured in accordance with ASTM Standard Method No. E1755-01 "Standard Method for the Determination of Ash in Biomass." This test method covers the determination of ash, expressed as the percentage of residue remaining after dry oxidation at 550 to 600° C. All results are reported relative to the 105° C. oven dry weight of the sample." See also: Sluiter, A. et al., "Determination of Ash in Biomass," National Renewable Energy Laboratory (NREL) Technical Report NREL/TP-510-42622, Jul. 17, 2005; and ASTM Standard Method No. E1755-01 "Standard Method for the Determination of Ash in Biomass," 2007, which are both incorporated herein by reference in their entirety.

As used herein, "degree of polymerization" refers to the number of monomeric units in a macromolecule or polymer or oligomer molecule, including those monomeric units that are not identical (such as in a oligomer with different monomeric residues). The degree of polymerization (DP) of the various saccharides in the compositions of the invention may be measured using gel permeation chromatography (GPC), high pressure liquid chromatography (HPLC), such as DIONEX with an electrochemical detector, matrix-assisted laser desorption/ionization time-of-flight (MALDI-TOF) mass spectrometry, or other conventional molecular weight determination methods.

C6 Saccharides

Accordingly, in one embodiment, the invention is directed to compositions, comprising C6 saccharides. In particular embodiments, the compositions comprise:
at least one water-soluble C6 oligosaccharide hydrolysate;
optionally, at least one water-soluble C6 monosaccharide hydrolysate; and
less than about 5250 ppm in total by weight, based on total weight of said water-soluble C6 oligosaccharide hydrolysate and said water-soluble C6 monosaccharide hydrolysate in said composition, of elements;
wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In certain embodiments, the elements are present at a level of less than about 5100 ppm in total by weight, based on total weight of said water-soluble C6 oligosaccharide hydrolysate and said water-soluble C6 monosaccharide hydrolysate in said composition.

In another embodiment, the invention is directed to compositions, comprising:
at least one water-soluble C6 oligosaccharide hydrolysate;
optionally, at least one water-soluble C6 monosaccharide hydrolysate; and
less than about 10 ppm by weight, based on total weight of said water-soluble C6 oligosaccharide hydrolysate and said water-soluble C6 monosaccharide hydrolysate in said composition, of aluminum;
less than about 3000 ppm by weight, based on total weight of said water-soluble C6 oligosaccharide hydrolysate and said water-soluble C6 monosaccharide hydrolysate in said composition, of calcium;
less than about 350 ppm by weight, based on total weight of said water-soluble C6 oligosaccharide hydrolysate and said water-soluble C6 monosaccharide hydrolysate in said composition, of iron; and
less than about 1000 ppm by weight, based on total weight of said water-soluble C6 oligosaccharide hydrolysate and said water-soluble C6 monosaccharide hydrolysate in said composition, of sulfur.

In certain preferred embodiments, such compositions further comprise:
less than about 5250 ppm in total by weight, based on total weight of said water-soluble C6 oligosaccharide hydrolysate and said water-soluble C6 monosaccharide hydrolysate in said composition, of elements;
wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In other embodiments, the invention is directed to compositions, comprising:
at least one water-soluble C6 oligosaccharide hydrolysate;
optionally, at least one water-soluble C6 monosaccharide hydrolysate; and
less than about 10 ppm by weight, based on total weight of said water-soluble C6 oligosaccharide hydrolysate and said water-soluble C6 monosaccharide hydrolysate in said composition, of aluminum.

In certain preferred embodiments, such compositions further comprise:
less than about 5250 ppm in total by weight, based on total weight of said water-soluble C6 oligosaccharide hydrolysate and said water-soluble C6 monosaccharide hydrolysate in said composition, of elements;
wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In a further embodiment, the invention is directed to compositions, comprising:
at least one water-soluble C6 oligosaccharide hydrolysate;
optionally, at least one water-soluble C6 monosaccharide hydrolysate; and
less than about 3000 ppm by weight, based on total weight of said water-soluble C6 oligosaccharide hydrolysate and said water-soluble C6 monosaccharide hydrolysate in said composition, of calcium.

In certain preferred embodiments, such compositions further comprise:
less than about 5250 ppm in total by weight, based on total weight of said water-soluble C6 oligosaccharide hydrolysate and said water-soluble C6 monosaccharide hydrolysate in said composition, of elements;
wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In yet other embodiments, the invention is directed to compositions, comprising:
at least one water-soluble C6 oligosaccharide hydrolysate;
optionally, at least one water-soluble C6 monosaccharide hydrolysate; and
less than about 350 ppm by weight, based on total weight of said water-soluble C6 oligosaccharide hydrolysate and said water-soluble C6 monosaccharide hydrolysate in said composition, of iron.

In certain preferred embodiments, such compositions further comprise:
less than about 5250 ppm in total by weight, based on total weight of said water-soluble C6 oligosaccharide hydrolysate and said water-soluble C6 monosaccharide hydrolysate in said composition, of elements;
wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In another embodiment, the invention is directed to compositions, comprising:
  at least one water-soluble C6 oligosaccharide hydrolysate;
  optionally, at least one water-soluble C6 monosaccharide hydrolysate; and
  less than about 1000 ppm by weight, based on total weight of said water-soluble C6 oligosaccharide hydrolysate and said water-soluble C6 monosaccharide hydrolysate in said composition, of sulfur.

In certain preferred embodiments, such compositions further comprise:
  less than about 5250 ppm in total by weight, based on total weight of said water-soluble C6 oligosaccharide hydrolysate and said water-soluble C6 monosaccharide hydrolysate in said composition, of elements;
  wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In certain embodiments, the water-soluble C6 oligosaccharide hydrolysate has a degree of polymerization of about 2 to about 15. In other embodiments, water-soluble C6 oligosaccharide hydrolysate has a degree of polymerization of about 2 to about 13. In other embodiments, water-soluble C6 oligosaccharide hydrolysate has a degree of polymerization of about 2 to about 10. In other embodiments, water-soluble C6 oligosaccharide hydrolysate has a degree of polymerization of about 2 to about 6.

In certain embodiments, the compositions further comprise at least one water-soluble C6 monosaccharide hydrolysate.

In certain embodiments, the water-soluble C6 monosaccharide hydrolysate is glucose, galactose, mannose, fructose, or a mixture thereof.

In certain embodiments, the compositions further comprise less than about 10 ppm, based on total weight of said water-soluble C6 oligosaccharide hydrolysate and said water-soluble C6 monosaccharide hydrolysate in said composition, of aluminum, preferably less than about 5 ppm by weight, based on total weight of said water-soluble C6 oligosaccharide hydrolysate and said water-soluble C6 monosaccharide hydrolysate in said composition, of aluminum.

In certain embodiments, the compositions further comprise less than about 3000 ppm by weight, based on total weight of said water-soluble C6 oligosaccharide hydrolysate and said water-soluble C6 monosaccharide hydrolysate in said composition, of calcium, preferably less than about 2950 ppm by weight, based on total weight of said water-soluble C6 oligosaccharide hydrolysate and said water-soluble C6 monosaccharide hydrolysate in said composition, of calcium.

In certain embodiments, the compositions further comprise less than about 350 ppm by weight, based on total weight of said water-soluble C6 oligosaccharide hydrolysate and said water-soluble C6 monosaccharide hydrolysate in said composition, of iron, preferably less than about 325 ppm by weight, based on total weight of said water-soluble C6 oligosaccharide hydrolysate and said water-soluble C6 monosaccharide hydrolysate in said composition, of iron.

In certain embodiments, the compositions further comprise less than about 1000 ppm by weight, based on total weight of said water-soluble C6 oligosaccharide hydrolysate and said water-soluble C6 monosaccharide hydrolysate in said composition, of sulfur, preferably less than about 975 ppm by weight, based on total weight of said water-soluble C6 oligosaccharide hydrolysate and said water-soluble C6 monosaccharide hydrolysate in said composition, of sulfur.

In certain embodiments, wherein the ratio of the total weight of said water-soluble C6 oligosaccharide hydrolysate and said water-soluble C6 monosaccharide hydrolysate to said elements is greater than about 45:1, preferably greater than about 47:1.

In certain embodiments, the level of said elements are measured by inductively coupled plasma emission spectroscopy.

In other embodiments, the compositions less than about 1500 mg of nitrogen per kg of total weight of water-soluble C6 saccharides, preferably less than about 1450 of nitrogen per kg of total weight of water-soluble C6 saccharides. Nitrogen may be measured by thermal conductivity detection after combustion and reduction.

In yet other embodiments of the compositions, the weight ratio of the collective mass of hydrogen and nitrogen to mass of carbon present in said water-soluble C6 oligosaccharide hydrolysate and said water-soluble C6 monosaccharide hydrolysate is less than about 0.14. Carbon, hydrogen, and nitrogen levels may be measured by thermal conductivity detection after combustion and reduction.

In certain other embodiments, the compositions comprising the C6 saccharides further comprise less than a maximum of any of the elements, individually or in combination, in the table listed below:

| Element | Level less than about (ppm or mg of element/kg of C6 saccharides) |
| --- | --- |
| As | 0.5 |
| B | 0.7 |
| Ba | 2.6 |
| Be | 0.05 |
| Cd | 0.10 |
| Co | 0.05 |
| Cr | 0.17 |
| Cu | 1.2 |
| K | 130 |
| Li | 0.05 |
| Mg | 180 |
| Mn | 15.0 |
| Mo | 0.7 |
| Na | 375 |
| Ni | 0.9 |
| P | 12.0 |
| Pb | 0.3 |
| Sb | 0.3 |
| Se | 0.6 |
| Si | 85.0 |
| Sn | 0.25 |
| Sr | 5.0 |
| Ti | 0.05 |
| Tl | 0.7 |
| V | 0.05 |
| Zn | 65 |

In another embodiment, the compositions comprise:
  about 80% by weight to about 95% by weight, based on total weight of C6 saccharides present in said composition, of water-soluble C6 oligosaccharides;
  wherein said water-soluble C6 oligosaccharides have a degree of polymerization of about 2 to about 15.

In certain embodiments, said water-soluble C6 oligosaccharides are present at a level of about 80% by weight to about 92.5% by weight, based on total weight of C6 saccharides present in said composition. In certain embodiments of the composition, said water-soluble C6 oligosaccharides have a degree of polymerization of about 2 to about 13, preferably, about 2 to about 10, and more preferably about 2 to about 6. In certain embodiments, the compositions further comprise about 5% by weight to about 20% by weight, based on total weight of C6 saccharides present in said composition, of C6 monosaccharides.

In certain embodiments of the compositions described herein, said water-soluble C6 oligosaccharide hydrolysate comprises:

about 10% by weight to about 25% by weight, based on total weight of said water-soluble C6 oligosaccharide hydrolysate and said water-soluble C6 monosaccharide hydrolysate in said composition, of C6 disaccharides;

about 10% by weight to about 25% by weight, based on total weight of said water-soluble C6 oligosaccharide hydrolysate and said water-soluble C6 monosaccharide hydrolysate in said composition, of C6 trisaccharides;

about 10% by weight to about 25% by weight, based on total weight of said water-soluble C6 oligosaccharide hydrolysate and said water-soluble C6 monosaccharide hydrolysate in said composition, of C6 tetrasaccharides;

about 10% by weight to about 25% by weight, based on total weight of said water-soluble C6 oligosaccharide hydrolysate and said water-soluble C6 monosaccharide hydrolysate in said composition, of C6 pentasaccharides; and about 10% by weight to about 50% by weight, based on total weight of said water-soluble C6 oligosaccharide hydrolysate and said water-soluble C6 monosaccharide hydrolysate in said composition, of C6 saccharides having at a degree of polymerization of at least about 6.

In certain embodiments, the compositions further comprise:

about 5% by weight to about 20% by weight, based on total weight of said water-soluble C6 oligosaccharide hydrolysate and said water-soluble C6 monosaccharide hydrolysate in said composition, of C6 monosaccharides.

In certain embodiments, the compositions further comprise:

about 7.5% by weight to about 20% by weight, based on total weight of said water-soluble C6 oligosaccharide hydrolysate and said water-soluble C6 monosaccharide hydrolysate in said composition, of C6 monosaccharides.

In other embodiments, the compositions comprise:

about 10% by weight to about 25% by weight, based on total weight of C6 saccharides present in said composition, of C6 disaccharides;

about 10% by weight to about 25% by weight, based on total weight of C6 saccharides present in said composition, of C6 trisaccharides;

about 10% by weight to about 25% by weight, based on total weight of C6 saccharides present in said composition, of C6 tetrasaccharides;

about 10% by weight to about 25% by weight, based on total weight of C6 saccharides present in said composition, of C6 pentasaccharides; and about 10% by weight to about 50% by weight, based on total weight of C6 saccharides present in said composition, of C6 saccharides having at a degree of polymerization of at least about 6.

In other embodiments of the compositions, said C6 disaccharides are present at a level of about 10% by weight to about 20% by weight, based on total weight of C6 saccharides present in said composition.

In other embodiments of the compositions, said C6 trisaccharides are present at a level of about 10% by weight to about 20% by weight, based on total weight of C6 saccharides present in said composition.

In other embodiments of the compositions, said C6 tetrasaccharides are present at a level of about 10% by weight to about 20% by weight, based on total weight of C6 saccharides present in said composition.

In other embodiments of the compositions, said C6 pentasaccharides are present at a level of about 10% by weight to about 20% by weight, based on total weight of C6 saccharides present in said composition.

In other embodiments of the compositions, said C6 saccharides having at a degree of polymerization of at least about 6 are present at a level of about 10% by weight to about 20% by weight, based on total weight of C6 saccharides present in said composition.

In other embodiments, the compositions further comprise:

about 5% by weight to about 20% by weight, based on total weight of said water-soluble C6 oligosaccharide hydrolysate and said water-soluble C6 monosaccharide hydrolysate in said composition, of C6 monosaccharides.

In certain embodiments, the compositions further comprise about 7.5% by weight to about 20% by weight, based on total weight of said water-soluble C6 oligosaccharide hydrolysate and said water-soluble C6 monosaccharide hydrolysate in said composition, of C6 monosaccharides.

In other embodiments, the compositions further comprise water.

In certain embodiments, the water-soluble C6 oligosaccharide hydrolysate and the water-soluble C6 monosaccharide hydrolysate are processed from lignocellulosic biomass using supercritical, subcritical, or near critical fluid extraction, or a combination thereof.

C5 Saccharides

Accordingly, in one embodiment, the invention is directed to compositions, comprising C5 oligosaccharides. In particular, the compositions comprise:

at least one water-soluble C5 oligosaccharide hydrolysate;

optionally, at least one water-soluble C5 monosaccharide hydrolysate; and less than about 3700 ppm in total by weight, based on total weight of said water-soluble C5 oligosaccharide hydrolysate and said water-soluble C5 monosaccharide hydrolysate in said composition, of elements;

wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In one embodiment, the invention is directed to compositions, comprising:

at least one water-soluble C5 oligosaccharide hydrolysate;

optionally, at least one water-soluble C5 monosaccharide hydrolysate; and less than about 10 ppm by weight, based on total weight of said water-soluble C5 oligosaccharide hydrolysate and said water-soluble C5 monosaccharide hydrolysate in said composition, of aluminum;

less than about 2300 ppm by weight, based on total weight of said water-soluble C5 oligosaccharide hydrolysate and said water-soluble C5 monosaccharide hydrolysate in said composition, of calcium;

less than about 50 ppm by weight, based on total weight of said water-soluble C5 oligosaccharide hydrolysate and said water-soluble C5 monosaccharide hydrolysate in said composition, of iron; and less than about 150 ppm by weight, based on total weight of said water-soluble C5 oligosaccharide hydrolysate and said water-soluble C5 monosaccharide hydrolysate in said composition, of sulfur.

In certain embodiments, the elements are present at a level of less than about 3610 ppm in total by weight, based on total weight of said water-soluble C5 oligosaccharide hydrolysate and said water-soluble C5 monosaccharide hydrolysate in said composition.

In further embodiments, the invention is directed to compositions, comprising:
- at least one water-soluble C5 oligosaccharide hydrolysate;
- optionally, at least one water-soluble C5 monosaccharide hydrolysate; and
- less than about 10 ppm by weight, based on total weight of said water-soluble C5 oligosaccharide hydrolysate and said water-soluble C5 monosaccharide hydrolysate in said composition, of aluminum.

In yet further embodiments, the invention is directed to compositions, comprising:
- at least one water-soluble C5 oligosaccharide hydrolysate;
- optionally, at least one water-soluble C5 monosaccharide hydrolysate; and
- less than about 2300 ppm by weight, based on total weight of said water-soluble C5 oligosaccharide hydrolysate and said water-soluble C5 monosaccharide hydrolysate in said composition, of calcium.

In another embodiment, the invention is directed to compositions, comprising:
- at least one water-soluble C5 oligosaccharide hydrolysate;
- optionally, at least one water-soluble C5 monosaccharide hydrolysate; and
- less than about 50 ppm by weight, based on total weight of said water-soluble C5 oligosaccharide hydrolysate and said water-soluble C5 monosaccharide hydrolysate in said composition, of iron.

In yet another embodiment, the invention is directed to compositions, comprising:
- at least one water-soluble C5 oligosaccharide hydrolysate;
- optionally, at least one water-soluble C5 monosaccharide hydrolysate; and
- less than about 150 ppm by weight, based on total weight of said water-soluble C5 oligosaccharide hydrolysate and said water-soluble C5 monosaccharide hydrolysate in said composition, of sulfur.

In certain embodiments, the compositions described herein further comprise:
- less than about 3700 ppm by weight in total, based on total weight of said water-soluble C5 oligosaccharide hydrolysate and said water-soluble C5 monosaccharide hydrolysate in said composition, of elements;
- wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In certain embodiments, the water-soluble C5 oligosaccharide hydrolysate has a degree of polymerization of at least about 2 to about 28. In other embodiments, water-soluble C5 oligosaccharide hydrolysate has a degree of polymerization of at least about 2 to about 15. In other embodiments, water-soluble C5 oligosaccharide hydrolysate has a degree of polymerization of at least about 2 to about 10. In other embodiments, water-soluble C5 oligosaccharide hydrolysate has a degree of polymerization of at least about 2 to about 6.

In certain embodiments, the compositions further comprise:
- at least one water-soluble C5 monosaccharide hydrolysate.

In certain embodiments, the water-soluble C5 monosaccharide hydrolysate is xylose, arabinose, lyxose, ribose, or a mixture thereof.

In certain embodiments, the compositions further comprise less than about 10 ppm by weight, based on total weight of said water-soluble C5 oligosaccharide hydrolysate and said water-soluble C5 monosaccharide hydrolysate in said composition, of aluminum, preferably less than about 5 ppm by weight, based on total weight of said water-soluble C5 oligosaccharide hydrolysate and said water-soluble C5 monosaccharide hydrolysate in said composition, of aluminum.

In certain embodiments, the compositions further comprise less than about 2300 ppm by weight, based on total weight of said water-soluble C5 oligosaccharide hydrolysate and said water-soluble C5 monosaccharide hydrolysate in said composition, of calcium, preferably less than about 2250 ppm by weight, based on total weight of said water-soluble C5 oligosaccharide hydrolysate and said water-soluble C5 monosaccharide hydrolysate in said composition, of calcium.

In certain embodiments, the compositions further comprise less than about 50 ppm by weight, based on total weight of said water-soluble C5 oligosaccharide hydrolysate and said water-soluble C5 monosaccharide hydrolysate in said composition, of iron, preferably less than about 30 ppm by weight, based on total weight of said water-soluble C5 oligosaccharide hydrolysate and said water-soluble C5 monosaccharide hydrolysate in said composition, of iron.

In certain embodiments, the compositions further comprise less than about 150 ppm by weight, based on total weight of said water-soluble C5 oligosaccharide hydrolysate and said water-soluble C5 monosaccharide hydrolysate in said composition, of sulfur, preferably less than about 140 ppm by weight, based on total weight of said water-soluble C5 oligosaccharide hydrolysate and said water-soluble C5 monosaccharide hydrolysate in said composition, of sulfur.

In certain embodiments, the ratio of total weight of said water-soluble C5 oligosaccharide hydrolysate and said water-soluble C5 monosaccharide hydrolysate in said composition to said elements is greater than about 75:1, preferably greater than about 80:1.

In certain embodiments, the water-soluble C5 oligosaccharide hydrolysate is processed from lignocellulosic biomass using supercritical, subcritical, or near critical fluid extraction, or a combination thereof.

In certain embodiments, the level of said elements are measured by inductively coupled plasma emission spectroscopy.

In other embodiments, the compositions comprise less than about 350 ppm of nitrogen per kg of total weight of water-soluble C5 saccharides, preferably less than about 325 ppm of nitrogen per kg of total weight of water-soluble C5 saccharides. Nitrogen may be measured by thermal conductivity detection after combustion and reduction.

In yet other embodiments of the compositions, the weight ratio of the collective mass of hydrogen and nitrogen to mass of carbon present in said water-soluble C5 oligosaccharide hydrolysate and said water-soluble C5 monosaccharide hydrolysate is less than about 0.14. Carbon, hydrogen, and nitrogen levels may be measured by thermal conductivity detection after combustion and reduction.

In certain other embodiments, the compositions comprising the C5 saccharides further comprise less than a maximum of any of the elements, individually or in combination, in the table listed below:

| Element | Level less than about (ppm or mg of element/kg of C5 saccharides) |
|---|---|
| As | 0.7 |
| B | 2.5 |
| Ba | 4.2 |

-continued

| Element | Level less than about (ppm or mg of element/kg of C5 saccharides) |
|---|---|
| Be | 0.02 |
| Cd | 0.2 |
| Co | 0.1 |
| Cr | 0.2 |
| Cu | 0.70 |
| K | 350 |
| Li | 0.05 |
| Mg | 550 |
| Mn | 130 |
| Mo | 0.5 |
| Na | 50 |
| Ni | 0.75 |
| P | 95 |
| Pb | 0.5 |
| Sb | 0.5 |
| Se | 0.75 |
| Si | 25 |
| Sn | 0.5 |
| Sr | 15 |
| Ti | 0.02 |
| Tl | 0.75 |
| V | 0.02 |
| Zn | 20 |

In another embodiment, the compositions comprise:

about 75% by weight to about 90% by weight, based on total weight of said water-soluble C5 oligosaccharide hydrolysate and said water-soluble C5 monosaccharide hydrolysate in said composition, of water-soluble C5 oligosaccharides;

wherein said water-soluble C5 oligosaccharides have a degree of polymerization of about 2 to about 28.

In certain embodiments, said water-soluble C5 oligosaccharides are present at a level of about 80% by weight to about 90% by weight, based on total weight of said water-soluble C5 oligosaccharide hydrolysate and said water-soluble C5 monosaccharide hydrolysate in said composition. In certain embodiments of the composition, said water-soluble C5 oligosaccharides have a degree of polymerization of about 2 to about 16, preferably, about 2 to about 10, and more preferably, about 2 to about 5. In certain embodiments, the compositions further comprise about 10% by weight, to about 25% by weight, based on total weight of said water-soluble C5 oligosaccharide hydrolysate and said water-soluble C5 monosaccharide hydrolysate in said composition, of C5 monosaccharides.

In certain embodiments of the compositions described herein, said water-soluble C5 oligosaccharide hydrolysate comprises:

about 15% by weight, to about 30% by weight, based on total weight of said water-soluble C5 oligosaccharide hydrolysate and said water-soluble C5 monosaccharide hydrolysate in said composition, of C5 disaccharides;

about 10% by weight, to about 20% by weight, based on total weight of said water-soluble C5 oligosaccharide hydrolysate and said water-soluble C5 monosaccharide hydrolysate in said composition, of C5 trisaccharides;

about 5% by weight, to about 20% by weight, based on total weight of said water-soluble C5 oligosaccharide hydrolysate and said water-soluble C5 monosaccharide hydrolysate in said composition, of C5 tetrasaccharides;

about 2% by weight, to about 20% by weight, based on total weight of said water-soluble C5 oligosaccharide hydrolysate and said water-soluble C5 monosaccharide hydrolysate in said composition, of C5 pentasaccharides; and about 10% by weight, to about 35% by weight, based on total weight of said water-soluble C5 oligosaccharide hydrolysate and said water-soluble C5 monosaccharide hydrolysate in said composition, of C5 saccharides having at a degree of polymerization of at least about 6.

In certain embodiments of the composition, said water-soluble C5 oligosaccharides have a degree of polymerization of about 2 to about 16, preferably, about 2 to about 10, and more preferably, about 2 to about 5. In certain embodiments, the compositions further comprise about 10% by weight, to about 25% by weight, based on total weight of said water-soluble C5 oligosaccharide hydrolysate and said water-soluble C5 monosaccharide hydrolysate in said composition, of C5 monosaccharides. In certain embodiments, the compositions further comprise about 12.5% by weight, to about 20% by weight, based on total weight of said water-soluble C5 oligosaccharide hydrolysate and said water-soluble C5 monosaccharide hydrolysate in said composition, of C5 monosaccharides.

In certain embodiments of the compositions described herein, said C5 disaccharides are present at a level of about 17.5% by weight to about 25% by weight, based on total weight of said water-soluble C5 oligosaccharide hydrolysate and said water-soluble C5 monosaccharide hydrolysate in said composition.

In certain embodiments of the compositions described herein, said C5 trisaccharides are present at a level of about 12.5% by weight to about 17.5% by weight, based on total weight of said water-soluble C5 oligosaccharide hydrolysate and said water-soluble C5 monosaccharide hydrolysate in said composition.

In certain embodiments of the compositions described herein, said C5 tetrasaccharides are present at a level of about 10% by weight to about 20% by weight, based on total weight of said water-soluble C5 oligosaccharide hydrolysate and said water-soluble C5 monosaccharide hydrolysate in said composition.

In certain embodiments of the compositions described herein, said C5 pentasaccharides are present at a level of about 2.5% by weight to about 15% by weight, based on total weight of said water-soluble C5 oligosaccharide hydrolysate and said water-soluble C5 monosaccharide hydrolysate in said composition.

In certain embodiments of the compositions described herein, said C5 saccharides having at a degree of polymerization of at least about 6 are present at a level of about 12.5% by weight to about 30% by weight, based on total weight of said water-soluble C5 oligosaccharide hydrolysate and said water-soluble C5 monosaccharide hydrolysate in said composition.

In certain embodiments, the compositions described herein further comprise about 10% by weight, to about 25% by weight, based on total weight of said water-soluble C5 oligosaccharide hydrolysate and said water-soluble C5 monosaccharide hydrolysate in said composition, of C5 monosaccharides.

In certain embodiments, the compositions described herein further comprise water.

In certain embodiments, the water-soluble C6 oligosaccharide hydrolysate and the water-soluble C6 monosaccharide hydrolysate are processed from lignocellulosic biomass using supercritical, subcritical, or near critical fluid extraction, or a combination thereof.

Further Embodiments

In certain embodiments, the invention is directed to methods of reducing the level of enzyme required for enzymatically hydrolyzing first water-soluble C6 saccharides having an average degree of polymerization to about 2 to about 15, preferably about 2 to about 10, and more preferably about 2 to about 6, to second water-soluble C6 saccharides having a lower average degree of polymerization than said average degree of polymerization of said first water-soluble C6 saccharides, comprising:

providing a hydrolysate comprising said first water-soluble C6 saccharides and less than about 5250 ppm in total, based on total weight of water-soluble C6 saccharide hydrolysate in said composition, of elements;

wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In certain embodiments, the C6 saccharides are extracted from lignocellulosic biomass. In other embodiments, the C6 saccharides are processed from lignocellulosic biomass using supercritical, subcritical, or near critical fluid extraction, or a combination thereof.

In certain embodiments, the invention is directed to methods of reducing the level of enzyme required for enzymatically hydrolyzing first water-soluble C5 saccharides having an average degree of polymerization to about 2 to about 28, preferably about 2 to about 15, more preferably about 2 to about 13, even more preferably about 2 to about 6, to second water-soluble C5 saccharides having a lower average degree of polymerization than said average degree of polymerization of said first water-soluble C5 saccharides, comprising:

providing a hydrolysate comprising said first water-soluble C5 saccharides and less than about 3700 ppm in total, based on total weight of water-soluble C5 saccharide hydrolysate in said composition, of elements;

wherein said elements are Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn.

In further embodiments, the compositions further comprise less than about 0.5% by weight, based on the total weight of said C5 saccharides or C6 saccharides, of organic solvent, such as alcohols, including water miscible lower aliphatic $C_1$-$C_4$ alcohols (e.g., methanol, ethanol, isopropanol, t-butanol). In preferred embodiments, the compositions contain less than about 0.1% by weight, based on the total weight of said of said C5 saccharides or C6 saccharides of organic solvent. In more preferred embodiments, the compositions contain substantially no organic solvent.

The compositions of the invention are preferably prepared from biomass by processes employing supercritical, subcritical, and/or near critical water, preferably without the addition of acid. The processes may include pretreatment step or steps using supercritical or near critical water to separate the C5 sugars (monomers and/or oligomers) from cellulose and lignin. In the pretreatment step, suitable temperatures are about 130° C. to about 250° C., suitable pressures are about 4 bars to about 100 bars, and suitable residence times are about 0.5 minutes to about 5 hours. The processes may also include a cellulose hydrolysis step or steps using supercritical or near critical water to separate the cellulose (which may processed to form C6 monomeric and/or oligomeric sugars) from the lignin. In the hydrolysis step(s), suitable temperatures are about 250° C. to about 450° C., suitable pressures are about 40 bars to about 260 bars, and suitable residence times are about 0.1 seconds to about 3 minutes. The compositions may be prepared in any suitable reactor, including, but not limited to, a tubular reactor, a digester (vertical, horizontal, or inclined), or the like. Suitable digesters include the digester system described in U.S. Pat. No. 8,057,639, which include a digester and a steam explosion unit, the entire disclosure of which is incorporated by reference.

The compositions of the invention comprising C5 saccharides or C6 saccharides may be utilized in a wide variety of applications, where C5 and C6 sugars are conventionally utilized, including, but not limited to, the production of various chemicals and fuels using fermentative, enzymatic, catalytic, and non-catalytic (e.g., thermal decomposition) processes. Such processes are useful for preparing feedstocks for the preparation of the following non-exhaustive list:

fuels (such as gasoline, jet fuel, butanol, and the like);

chemicals (such as acetic acid, acetic anhydride, acetone, acrylic acid, adipic acid, benzene, ethanol, ethylene, ethylene glycol, ethylene oxide, methanol, polypropylene, terephthalic acid, toluene, xylene, 1,3-propanediol, 1,4-butanediol, and the like);

pharmaceuticals and foods (such as acetoin, alanine, arabitol, ascorbic acid, aspartic acid, citric acid, coumaric acid, fumaric acid, glycerol, glycine, kojic acid, lactic acid, lysine, malonic acid, proline, propionic acid, serine, sorbitol, succinic acid, threonine, xylitol, sugar acids (glucaric acid, gluconic acid, xylonic acids), and the like);

specialty chemicals (such as acontic acid, glutamic acid, malic acid, oxalic acid, and the like);

textile applications (such as formic acid and the like); and industrial intermediates (acetaldehyde, 3-hydroxypropionic acid, 2,5-furan dicarboxylic acid, furfural, glutaric acid, itaconic acid, levulinic acid, and the like).

The present invention is further defined in the following Examples, in which all parts and percentages are by weight, unless otherwise stated. It should be understood that these examples, while indicating preferred embodiments of the invention, are given by way of illustration only and are not to be construed as limiting in any manner. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1: Preparation of Oligosaccharide Compositions

The C5 oligosaccharide and C6 oligosaccharide compositions of the invention were prepared using supercritical, subcritical, and near critical water extraction in a two stage process. Particulate lignocellulosic biomass consisting of mixed hardwood chips of 140 mesh or less was mixed with water to form a slurry (about 20% by weight solids). The slurry was heated to a temperature of about 170-245° C. and then feed into a pretreatment reactor for about 1-120 minutes under sufficient pressure to keep the water in the liquid phase. The pretreated slurry was then cooled to a temperature less than about 100° C. under little (less than about 10 bar) or no pressure. The pretreated solids were then separated from the liquid stream using a filter press. Alternatively, the solids may be separated using a centrifugal filter pressor. The pretreated solids were then mixed with water to form a slurry and the slurry was heated to a temperature of about 150-250° C. The slurry was then subjected to supercritical water at about 374-600° C. in a hydrolysis reactor for about 0.05-10 seconds under a pressure of about 230-300 bar. After exiting the hydrolysis reactor, the hydrolyzed slurry was quenched with water and then flashed to about ambient temperature and pressure to remove water. The lignin solids were then separated from the liquid stream using a centrifugal decanter and air dried.

The C5 oligosaccharides and the C6 oligosaccharides streams were first concentrated to about 200 g/L, adjusted to about pH 3-4 and filtered using 0.45 micron filter.

Example 2: Analysis of Oligosaccharide Compositions Using Inductively Coupled Plasma The dried compositions containing the C5 and C6 oligosaccharides of Example 1 were analyzed using inductively coupled plasma emission spectroscopy. The results are shown in the table below:

| Species | Oligomer (C6) g/liter or ppm | Oligomer (C5) g/liter or ppm |
| --- | --- | --- |
| Al | 4.63 | 4.05 |
| As | 0.39 | 0.54 |
| B | 0.61 | 2.31 |
| Ba | 2.49 | 3.94 |
| Be | 0.00 | 0.01 |
| Ca | 2945.00 | 2245.00 |
| Cd | 0.05 | 0.11 |
| Co | 0.04 | 0.08 |
| Cr | 0.14 | 0.12 |
| Cu | 0.97 | 0.70 |
| Fe | 309.00 | 22.94 |
| K | 127.35 | 329.00 |
| Li | 0.03 | 0.02 |
| Mg | 178.00 | 545.50 |
| Mn | 14.40 | 126.40 |
| Mo | 0.58 | 0.32 |
| Na | 368.50 | 44.80 |
| Ni | 0.78 | 0.69 |
| P | 10.99 | 90.20 |
| Pb | 0.21 | 0.32 |
| S | 946.00 | 132.45 |
| Sb | 0.21 | 0.30 |
| Se | 0.45 | 0.66 |
| Si | 80.65 | 22.10 |
| Sn | 0.18 | 0.39 |
| Sr | 3.51 | 13.66 |
| Ti | 0.00 | 0.00 |
| Tl | 0.45 | 0.67 |
| V | 0.02 | 0.01 |
| Zn | 61.35 | 17.48 |

Example 3: Analysis of Oligosaccharide Compositions Using Gel Permeation Chromatography The C5 oligosaccharide and C6 oligosaccharide compositions of the invention were prepared using supercritical, subcritical, and near critical water extraction in a two stage process as described in Example 1. The samples were then diluted ten times. The degree of polymerization was qualitatively determined, i.e., not quantifying the amount of each oligomer, using gel permeation chromatography.

Figure 1B:
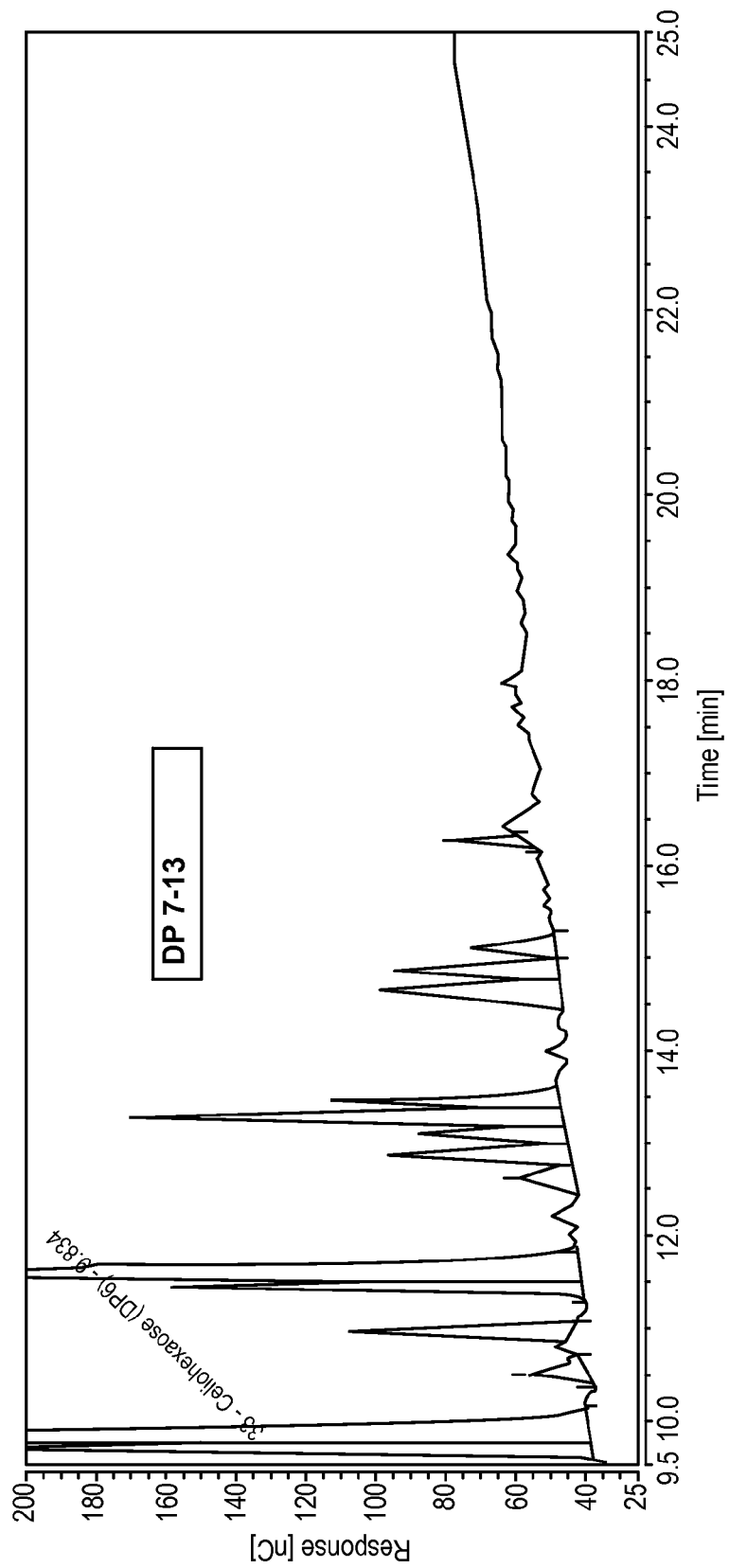
FIG. 1B is a scan from a DIONEX high pressure liquid chromatography device with an electrochemical detector of a C6 oligosaccharide composition of one embodiment of the invention.
Figure 2A:
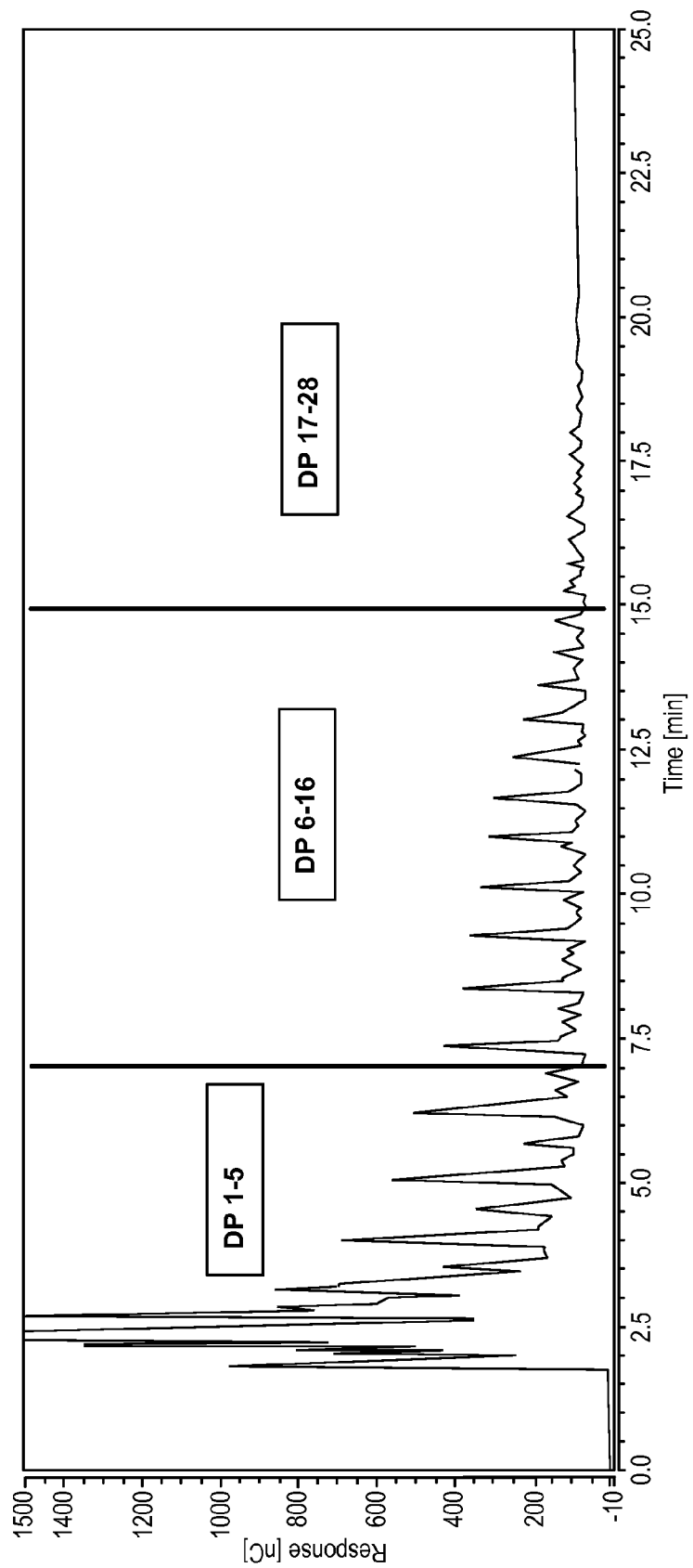
FIG. 2A is a scan from a DIONEX high pressure liquid chromatography device with an electrochemical detector of a C5 oligosaccharide composition of one embodiment of the invention.
Figure 2B:
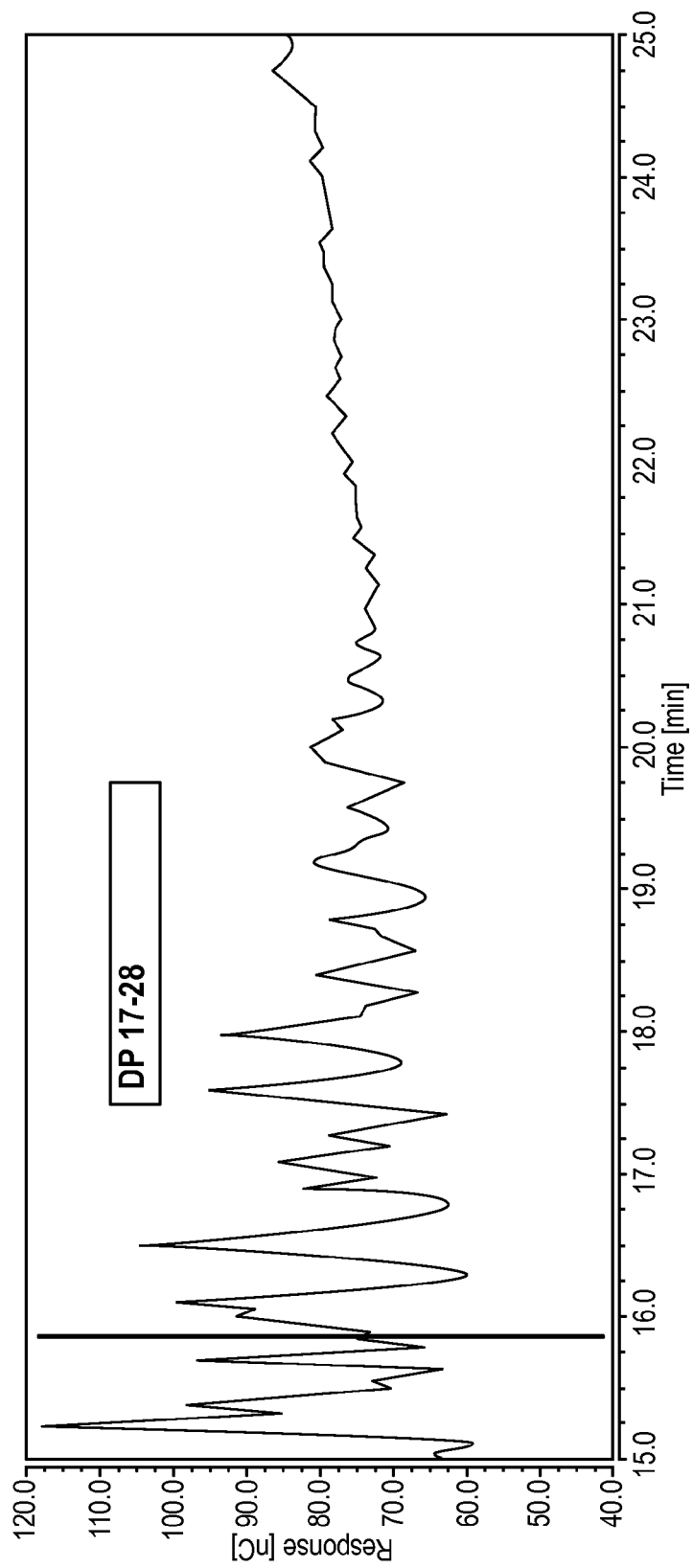
FIG. 2B is a scan from a DIONEX high pressure liquid chromatography device with an electrochemical detector of a C5 oligosaccharide composition of one embodiment of the invention.

As can be seen in FIGS. 1A and 1B, a degree of polymerization (DP) were detected up to at least a DP of 13, with small peaks visible above DP of 13 for the C6 oligosaccharide compositions. As can be seen in FIGS. 2A and 2B, a degree of polymerization (DP) were detected up to at least a DP of 28, with small peaks visible above DP of 28 for the C5 oligosaccharide compositions.

Example 4: Analysis of C6 Saccharide Compositions Using Gel Permeation Chromatography The C6 saccharide compositions of the invention were prepared using supercritical, subcritical, and near critical water extraction in a two stage process as described in Example 1. Representative samples bracketing the extremes/possibilities of feed material source (tubular reactor), reactor temperature (348.2-383.4° C.), reactor residence time (0.19-1.48 seconds), and feed aqueous slurry concentration (6.4-14.77%) were selected.

The representative samples were analyzed using gel permeation chromatography. The area under each peak (indicating an individual mer unit in the saccharide) was measured to calculate weight % of each mer unit, based on the total weight of C6 saccharides present in the sample. The results are shown in the following table:

| Sample | C6 mono-saccharides (weight %) | C6 disac-charides (weight %) | C6 trisac-charides (weight %) | C6 tetrsac-charides (weight %) | C6 pentasac-charides (weight %) | C6 hexasac-charides + (weight %) |
| --- | --- | --- | --- | --- | --- | --- |
| 1-1033 | 15.3 | 19.8 | 15.4 | 15.2 | 12.1 | 22.2 |
| 2-1448 | 19.3 | 19.1 | 18.9 | 15.6 | 14.7 | 12.4 |
| 3-1252 | 8.9 | 11.3 | 13.3 | 12.4 | 16.6 | 37.5 |
| 4-2125 | 16.8 | 17.1 | 17.1 | 15.4 | 15.9 | 17.8 |
| 5-2344 | 13.689 | 16.444 | 15.454 | 14.945 | 12.652 | 26.816 |
| 6-1600 | 7.914 | 10.087 | 11.397 | 13.024 | 12.71 | 44.867 |

Example 5: Analysis of C5 Saccharide Compositions Using Gel Permeation Chromatography The C5 saccharide compositions of the invention were prepared using supercritical, subcritical, and near critical water extraction in the first stage of the two stage process as described in Example 1. Representative samples bracketing the extremes/possibilities of reactor feed concentration (10.66-13.78 weight %, reactor temperature (249-261° C.), and reactor residence time (2-3 minutes) were selected.

The representative samples were analyzed using gel permeation chromatography (details below).

GPC Agilent HPLC System Configuration

| | |
|---|---|
| Auto Sampler | 1260 ASL |
| Pump | 1260 isocratic pump Agilent |
| Heater | 1260 TCC |
| Degasser | 1260 degasser |
| Mobile Phase | DI water |
| Column | Ultrahydrogel-120, 250, 500 from Waters (injection vol 25 μl, Size 7.8 × 300 mm) temp 30° C. |
| Flow Rate | 0.5 ml/min; run time of 80 minutes |
| Detector | 1260-RID set at 50° C. Agilent and DAD (signal 214 and 270 nm) |

The area under each peak (indicating an individual mer unit in the saccharide) was measured to calculate weight % of each mer unit, based on the total weight of C5 saccharides present in the sample. The results are shown in the following table:

| Sample | C5 monosaccharides (weight %) | C5 disaccharides (weight %) | C5 trisaccharides (weight %) | C5 tetrsaccharides (weight %) | C5 pentasaccharides (weight %) | C5 ≥ hexasaccharides (weight %) |
|---|---|---|---|---|---|---|
| 7-0458 | 18.2 | 24.4 | 16.3 | 14.1 | 11.8 | 15.3 |
| 8-0550 | 17.0 | 21.8 | 16.2 | 11.6 | 13.0 | 20.3 |
| 9-0647 | 16.1 | 23.5 | 18.1 | 10.7 | 4.5 | 27.1 |
| 10-2144 | 17.2 | 23.6 | 17.6 | 10.4 | 9.4 | 21.9 |
| 11-2242 | 13.3 | 20.4 | 13.9 | 17.4 | 9.3 | 25.4 |
| 12-2348 | 13.4 | 19.3 | 14.7 | 13.0 | 9.5 | 30.1 |

Example 6: Analysis of C5 and C6 Saccharide Compositions Using HPLC with an Electrochemical Detector The C5 and C6 saccharide compositions of the invention were prepared using supercritical, subcritical, and near critical water extraction in the two stage process as described in Example 1. Representative samples were selected.

The representative samples were analyzed using DIONEX HPLC (details below).

Dionex System Thermo Scientific Configuration

| | |
|---|---|
| Auto Sampler | AS-AP |
| Pump | ICS-5000 DP (dual pulse) |
| Mobile Phase | 100 mM NaOH (sodium hydrohyde) + deionized water |
| | 100 mM NaOH (sodium hydrohyde) + 1M NaOAc (sodium acetate) |
| Column/Heater | CarboPac PA 200 3 × 250 mm temp 30° C. with guard column CarboPac PA 200 3 × 250 mm (injection vol 10 μl) and compartment temperature 30° C. |
| Flow Rate | 0.5 ml/min; run time of 70 minutes |
| Detector | ICS-5000 DC Electro chemical detector |

The results are averaged and shown in the tables below:

| DIONEX averaged results (varying residence time in hemihydrolysis reactor; varying slurry loading) | | | | | | | | | | | | | |
|---|---|---|---|---|---|---|---|---|---|---|---|---|---|
| Residence time | Slurry loading | C5 monomer (xylose) | | C5 dimer | | C5 trimer | | C5 tetramer | | C5 pentamer | | C5 hexamer | |
| minutes | % | g/L | wt % | g/L | wt % | g/L | wt % | g/L | wt % | g/L | wt % | g/L | wt % |
| 2 | 11.39 | 0.28835 | 6.9 | 1.7517 | 42.0 | 1.4432 | 34.6 | 0.0981 | 2.4 | 0.1817 | 4.4 | 0.4095 | 9.8 |
| 3 | 10.95 | 0.91497 | 19.8 | 1.6926 | 36.7 | 1.248 | 27.0 | 0.35397 | 7.7 | 0.2271 | 4.9 | 0.18023 | 3.9 |

DIONEX averaged results
(varying slurry loading)

| Residence time | Slurry loading | C5 monomer (xylose) | | C5 dimer | | C5 trimer | | C5 tetramer | | C5 pentamer | | C5 hexamer | |
|---|---|---|---|---|---|---|---|---|---|---|---|---|---|
| minutes | % | g/L | wt % | g/L | wt % | g/L | wt % | g/L | wt % | g/L | wt % | g/L | wt % |
| 2 | 11.39 | 0.28835 | 6.9 | 1.7517 | 42.0 | 1.4432 | 34.6 | 0.0981 | 2.4 | 0.1817 | 4.4 | 0.4095 | 9.8 |
| 2 | 12.24 | 0.3272 | 6.5 | 2.1768 | 43.0 | 0.7087 | 14.0 | 1.3541 | 26.8 | 0.223 | 4.4 | 0.2685 | 5.3 |

DIONEX averaged results
(varying hemihydrolysis reactor total time)

| Residence time | Slurry loading | C5 monomer | | C5 dimer | | C5 trimer | | C5 tetramer | | C5 pentamer | | C5 hexamer | |
|---|---|---|---|---|---|---|---|---|---|---|---|---|---|
| hours | % | g/L | wt % | g/L | wt % | g/L | wt % | g/L | wt % | g/L | wt % | g/L | wt % |
| 1 | 10.95 | 1.7316 | 19.99 | 0.4674 | 5.4 | 3.1371 | 36.1 | 0.5831 | 6.7 | 0.0618 | 0.7 | 0.0139 | 0.2 |
| 2 | 10.95 | 0.489 | 13.5 | 2.2848 | 62.9 | 0.3536 | 9.7 | 0.2033 | 5.6 | 0.0679 | 1.9 | 0.2323 | 6.4 |
| 3 | 10.95 | 0.5243 | 12.4 | 2.3256 | 55.0 | 0.2533 | 6.0 | 0.2755 | 6.5 | 0.5516 | 13.1 | 0.2945 | 7.0 |

DIONEX averaged results
(with and without quench post cellulose hydrolysis)

| | Rx T | Total Flow Rate | C6 monomer (glucose) | | C6 dimer | | C6 trimer | | C6 tetramer | | C6 pentamer | | C6 hexamer | |
|---|---|---|---|---|---|---|---|---|---|---|---|---|---|---|
| | °C. | | g/L | wt % | g/L | wt % | g/L | wt % | g/L | wt % | g/L | wt % | g/L | wt % |
| With quench | 374.2 | 1049.9 | 2.9 | 24.2 | 1.8 | 14.9 | 1.7 | 14.3 | 1.7 | 13.8 | 2.2 | 18.4 | 1.7 | 14.3 |
| Without quench | 367.7 | 774.8 | 1.95 | 18.6 | 1.77 | 16.9 | 1.51 | 14.5 | 1.45 | 13.9 | 1.94 | 18.6 | 1.82 | 17.4 |

DIONEX averaged results
(with and without quench post cellulose hydrolysis; quench at 200° C.)

| | Rx T | Total Flow Rate | C6 monomer (glucose) | | C6 dimer | | C6 trimer | | C6 tetramer | | C6 pentamer | | C6 hexamer | |
|---|---|---|---|---|---|---|---|---|---|---|---|---|---|---|
| | °C. | | g/L | wt % | g/L | wt % | g/L | wt % | g/L | wt % | g/L | wt % | g/L | wt % |
| With quench | 383.4 | 766.6 | 0.9 | 25.5 | 0.6 | 15.5 | 0.6 | 16.9 | 0.5 | 13.7 | 0.5 | 14.9 | 0.5 | 13.5 |
| Without quench | 379.0 | 796.3 | 1.59 | 15.5 | 0.23 | 2.2 | 2.24 | 21.8 | 1.95 | 19.0 | 2.13 | 20.7 | 2.13 | 20.8 |

DIONEX averaged results
(residence time in reactor)

| | Rx T | Total Flow Rate | C6 monomer (glucose) | | C6 dimer | | C6 trimer | | C6 tetramer | | C6 pentamer | | C6 hexamer | |
|---|---|---|---|---|---|---|---|---|---|---|---|---|---|---|
| | °C. | | g/L | wt % | g/L | wt % | g/L | wt % | g/L | wt % | g/L | wt % | g/L | wt % |
| 0.19 seconds | 373.0 | 775.6 | 0.66 | 13.1 | 0.66 | 13.1 | 0.84 | 16.6 | 0.85 | 16.8 | 0.94 | 18.5 | 1.1059 | 21.9 |
| 1.22 seconds | 374.2 | 1049.9 | 2.94 | 24.2 | 1.81 | 14.9 | 1.73 | 14.3 | 1.67 | 13.8 | 2.24 | 18.4 | 1.74 | 14.3 |

DIONEX averaged results
(varying residence time in hemihydrolysis reactor; varying slurry loading)

| Residence time | Slurry loading | C5 monomer | | C5 dimer | | C5 trimer | | C5 tetramer | | C5 pentamer | | C5 hexamer | |
|---|---|---|---|---|---|---|---|---|---|---|---|---|---|
| minutes | % | g/L | wt % | g/L | wt % | g/L | wt % | g/L | wt % | g/L | wt % | g/L | wt % |
| 2 | 11.39 | 0.28835 | 6.9 | 1.7517 | 42.0 | 1.4432 | 34.6 | 0.0981 | 2.4 | 0.1817 | 4.4 | 0.4095 | 9.8 |
| 3 | 10.95 | 0.91497 | 19.8 | 1.6926 | 36.7 | 1.248 | 27.0 | 0.35397 | 7.7 | 0.2271 | 4.9 | 0.18023 | 3.9 |

When ranges are used herein for physical properties, such as molecular weight, or chemical properties, such as chemical formulae, all combinations, and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A composition, comprising: a water-soluble C5 oligosaccharide hydrolysate; and optionally, a water-soluble C5 monosaccharide hydrolysate; wherein said water-soluble C5 oligosaccharide hydrolysate comprises:
    12.5% by weight to about 17.5% by weight, based on total weight of water-soluble C5 oligosaccharide hydrolysate and water-soluble C5 monosaccharide hydrolysate, if present, in said composition, of C5 trisaccharides; and
    10% by weight to about 35% by weight based on total weight of water-soluble C5 oligosaccharide hydrolysate and water-soluble C5 monosaccharide hydrolysate, if present in said composition, of water-soluble C5 saccharides having a degree of polymerization of at least about 6.

2. The composition of claim 1, wherein said water-soluble C5 oligosaccharide hydrolysate comprises a C5 oligosaccharide having a degree of polymerization of at least about 2 to about 28.

3. The composition of claim 1, wherein said water-soluble C5 oligosaccharide hydrolysate comprises a C5 oligosaccharide having a degree of polymerization of at least about 2 to about 16.

4. The composition of claim 1, wherein said water-soluble C5 oligosaccharide hydrolysate comprises a C5 oligosaccharide having a degree of polymerization of at least about 2 to about 10.

5. The composition of claim 1, wherein said water-soluble C5 oligosaccharide hydrolysate comprises a C5 oligosaccharide having a degree of polymerization of at least about 2 to about 5.

6. The composition of claim 1, further comprising water.

7. The composition of claim 1, wherein said water-soluble C5 oligosaccharide hydrolysate is processed from lignocellulosic biomass using supercritical, subcritical, or near critical fluid extraction, or a combination thereof.

8. The composition of claim 1, wherein nitrogen, if present, comprises less than about 350 mg of nitrogen per kg of total weight of water-soluble C5 saccharides.

9. The composition of claim 1, wherein the weight ratio of collective mass of hydrogen and nitrogen to mass of carbon present in said water-soluble C5 oligosaccharide hydrolysate and said water-soluble C5 monosaccharide hydrolysate, if present, is less than about 0.14.

10. A composition of claim 1, wherein elements, if present, comprise a total amount by weight, based on total weight of said composition, of less than about 3700 ppm of elements Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn, when said composition is measured for all of said elements.

11. The composition of claim 10, wherein the ratio of the total weight of said water-soluble C5 oligosaccharide hydrolysate and said water-soluble C5 monosaccharide hydrolysate in said composition to said elements is greater than about 75:1.

12. The composition of claim 10, wherein levels of said elements is measured by inductively coupled plasma emission spectroscopy.

13. The composition of claim 1, wherein aluminum, calcium, iron and sulfur, if present, comprise, based on total weight of said composition, less than about 10 ppm by weight of aluminum; less than about 2300 ppm by weight of calcium; less than about 50 ppm by weight of iron; and less than about 150 ppm by weight of sulfur.

14. The composition of claim 13, wherein elements, if present, comprise a total amount by weight, based on total weight of said composition, of less than about 3700 ppm of elements Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn, when said composition is measured for all of said elements.

15. The composition of claim 1, wherein aluminum, if present, comprises less than about 10 ppm by weight of the composition.

16. The composition of claim 1, wherein calcium, if present, comprises less than about 2300 ppm by weight of the composition.

17. The composition of claim 1, wherein iron, if present, comprises less than about 50 ppm by weight of the composition.

18. The composition of claim 1, wherein sulfur, if present, comprises than about 150 ppm by weight of the composition.

19. The composition of claim 1, further comprising: at least one water-soluble C5 monosaccharide hydrolysate.

20. The composition of claim 19, wherein said at least one water-soluble C5 monosaccharide hydrolysate is xylose, arabinose, lyxose, ribose, or a mixture thereof.

21. The composition of claim 19, wherein aluminum, if present, comprises less than about 10 ppm by weight of the composition.

22. The composition of claim 19, wherein calcium, if present, comprises, less than about 2300 ppm by weight of the composition.

23. The composition of claim 19, wherein iron, if present, comprises less than about 50 ppm by weight of the composition.

24. The composition of claim 19, wherein sulfur, if present, comprises less than about 150 ppm by weight of the composition.

25. The composition of claim 19, wherein elements, if present, comprise a total amount by weight, based on total weight of said composition, of less than about 3700 ppm of elements Al, As, B, Ba, Be, Ca, Cd, Co, Cr, Cu, Fe, K, Li, Mg, Mn, Mo, Na, Ni, P, Pb, S, Sb, Se, Si, Sn, Sr, Ti, Tl, V, and Zn, when said composition is measured for all of said elements.

26. The composition of claim 1, wherein said water-soluble C5 oligosaccharide hydrolysate further comprises:
    about 15% by weight, to about 30% by weight, based on total weight of said water-soluble C5 oligosaccharide hydrolysate and said water-soluble C5 monosaccharide hydrolysate, if present, in said composition, of C5 disaccharides;
    about 5% by weight, to about 20% by weight, based on total weight of said water-soluble C5 oligosaccharide hydrolysate and said water-soluble C5 monosaccharide hydrolysate, if present, in said composition, of C5 tetrasaccharides; and
    about 2% by weight, to about 20% by weight, based on total weight of said water-soluble C5 oligosaccharide hydrolysate and said water-soluble C5 monosaccharide hydrolysate, if present, in said composition, of C5 pentasaccharides.

27. The composition of claim 26, wherein said water-soluble C5 monosaccharide hydrolysate is present at a level of about 10% by weight, to about 25% by weight, based on total weight of said water-soluble C5 oligosaccharide hydrolysate and said water-soluble C5 monosaccharide hydrolysate in said composition.

28. The composition of claim 26, further comprising water.

29. The composition of claim 1, wherein said water-soluble C5 monosaccharide hydrolysate is present at a level of about 10% by weight, to about 25% by weight, based on total weight of said water-soluble C5 oligosaccharide hydrolysate and said water-soluble C5 monosaccharide hydrolysate in said composition.

30. The composition of claim 1, wherein said C5 disaccharides are present at a level of 15% by weight to about 30% by weight, based on total weight of said water-soluble C5 oligosaccharide hydrolysate and said water-soluble C5 monosaccharide hydrolysate, if present, in said composition.

31. The composition of claim 1, wherein said C5 tetrasaccharides are present at a level of about 5% by weight to about 20% by weight, based on total weight of said water-soluble C5 oligosaccharide hydrolysate and said water-soluble C5 monosaccharide hydrolysate, if present, in said composition.

32. The composition of claim 1, wherein said C5 pentasaccharides are present at a level of about 2% by weight to about 20% by weight, based on total weight of said water-soluble C5 oligosaccharide hydrolysate and said water-soluble C5 monosaccharide hydrolysate, if present, in said composition.

33. The composition of claim 1, further comprising: about 75% by weight to about 90% by weight, based on total weight of said water-soluble C5 oligosaccharide hydrolysate and said water-soluble C5 monosaccharide hydrolysate, if present, in said composition, of water-soluble C5 oligosaccharides; wherein said water-soluble C5 oligosaccharides have a degree of polymerization of about 2 to about 16.

34. The composition of claim 33, wherein said water-soluble C5 oligosaccharides are present at a level of about 80% by weight to about 90% by weight, based on total weight of said water-soluble C5 oligosaccharide hydrolysate and said water-soluble C5 monosaccharide hydrolysate, if present, in said composition.

35. The composition of claim 33, wherein said water-soluble C5 oligosaccharides have a degree of polymerization of about 2 to about 10.

36. The composition of claim 33, wherein said water-soluble C5 oligosaccharides have a degree of polymerization of about 2 to about 5.

37. The composition of claim 33, further comprising: about 10% by weight to about 25% by weight, based on total weight of said water-soluble C5 oligosaccharide hydrolysate and said water-soluble C5 monosaccharide hydrolysate in said composition, of C5 monosaccharides.

38. The composition of claim 33, further comprising water.

* * * * *